(12) United States Patent
Docagne et al.

(10) Patent No.: US 10,072,077 B2
(45) Date of Patent: Sep. 11, 2018

(54) ANTIBODY USEFUL IN NEUROLOGICAL OR NEURODEGENERATIVE DISORDERS

(71) Applicants: PAION DEUTSCHLAND GMBH, Aachen (DE); INSERM, Paris (FR)

(72) Inventors: Fabian Docagne, Paris (FR); Richard Macrez, Paris (FR); Denis Vivien, Paris (FR); Karl-Uwe Petersen, Aachen (DE)

(73) Assignees: PAION DEUTSCHLAND, Aachen (DE); INSERM (INSTITUT NATIONAL DE LA SANTE ET DE LA RECHERCHE MEDICALE), Paris (FR); UNIVERSITE DE CAEN NORMANDIE, Caen (FR)

(*) Notice: Subject to any disclaimer, the term of this patent is extended or adjusted under 35 U.S.C. 154(b) by 0 days.

(21) Appl. No.: 14/890,613

(22) PCT Filed: May 21, 2014

(86) PCT No.: PCT/EP2014/060486
§ 371 (c)(1),
(2) Date: Nov. 12, 2015

(87) PCT Pub. No.: WO2014/187879
PCT Pub. Date: Nov. 27, 2014

(65) Prior Publication Data
US 2016/0115230 A1    Apr. 28, 2016

(30) Foreign Application Priority Data

May 21, 2013 (EP) .................................. 13002641
Jun. 3, 2013 (EP) .................................. 13002850

(51) Int. Cl.
*C07K 16/00* (2006.01)
*C07K 16/28* (2006.01)
*A61K 39/00* (2006.01)

(52) U.S. Cl.
CPC ............ *C07K 16/28* (2013.01); *C07K 16/286* (2013.01); *A61K 2039/505* (2013.01); *C07K 2317/34* (2013.01); *C07K 2317/565* (2013.01)

(58) Field of Classification Search
None
See application file for complete search history.

(56) References Cited

U.S. PATENT DOCUMENTS

2011/0263436 A1* 10/2011 Tu ..................... C07K 16/109
506/2

FOREIGN PATENT DOCUMENTS

WO    2011/023250 A1    3/2011

OTHER PUBLICATIONS

Paul, Fundamental Immunology, (textbook), 1993, pp. 292-295.*
Rudikoff et al (Proc Natl Acad Sci USA 1982 vol. 79 p. 1979).*
MacCallum et al. (J. Mol. Biol. (1996) 262:732-745).*
De Pascalis et al. (The Journal of Immunology (2002) 169, 3076-3084).*
Vajdos et al. ((2002) J. Mol. Biol. 320, 415-428).*
Wu et al. (1999, J. Mol. Biol. 294, 151-162).*
Gaberel et al., "Immunotherapy blocking the tissue plasminogen activator-dependent activation of N-methyl-d-aspartate glutamate receptors improves hemmorhagic stroke outcome", Neuropharmacology, Apr. 1, 2013, pp. 267-271, vol. 67.
Macrez et al., "Antibodies Preventing the Interaction of Tissue-Type Plasminogen Activator with N-Methyl-D-Aspartate Receptors Reduce Stroke Damages and Extend the Therapeutic Window of Thrombolysis", Stroke, Aug. 1, 2011, pp. 2315-2322, vol. 42, No. 8.
Fernandez-Monreal et al., "Arginine 260 of the amino-terminal domain of NR1 subunit is critical for tissue-type plasminogen activator-mediated enhancement of N-methyl-D-aspartate receptor signaling", Journal of Biological Chemistry, Dec. 3, 2004, pp. 50850-50856, vol. 279, No. 49.
Amrutkar et al., "-aspartate receptor reveals a short linear epitope", Biopolymers, Nov. 12, 2012, pp. 567-575, vol. 98, No. 6.
Anonymous, "Datasheet SC-9058", Internet Citation, Jan. 1, 2006, Web.

* cited by examiner

*Primary Examiner* — Daniel E Kolker
*Assistant Examiner* — Aditi Dutt
(74) *Attorney, Agent, or Firm* — Whitham & Cook, P.C.

(57) ABSTRACT

The present invention relates to an anti-NMDA antibody or fragment or derivative thereof which is effective in inhibiting the deleterious effects of tissue-type plasminogen activator (t-PA) mediated by N-methyl-D-aspartate (NMDA) receptors and to medical uses, in particular for the treatment of neurological or neurodegenerative disorders, e.g. multiple sclerosis.

8 Claims, 10 Drawing Sheets
Specification includes a Sequence Listing.

SEQUENCE LISTING

```
<160> NUMBER OF SEQ ID NOS: 44

<210> SEQ ID NO 1
<211> LENGTH: 3
<212> TYPE: PRT
<213> ORGANISM: Rattus sp.

<400> SEQUENCE: 1

Lys Arg Leu
1

<210> SEQ ID NO 2
<211> LENGTH: 4
<212> TYPE: PRT
<213> ORGANISM: Rattus sp.

<400> SEQUENCE: 2

Lys Arg Leu Glu
1

<210> SEQ ID NO 3
<211> LENGTH: 5
<212> TYPE: PRT
<213> ORGANISM: Rattus sp.

<400> SEQUENCE: 3

Lys Arg Leu Glu Thr
1               5

<210> SEQ ID NO 4
<211> LENGTH: 6
<212> TYPE: PRT
<213> ORGANISM: Rattus sp.

<400> SEQUENCE: 4

Lys Arg Leu Glu Thr Leu
1               5

<210> SEQ ID NO 5
<211> LENGTH: 7
<212> TYPE: PRT
<213> ORGANISM: Rattus sp.

<400> SEQUENCE: 5

Lys Arg Leu Glu Thr Leu Leu
1               5

<210> SEQ ID NO 6
<211> LENGTH: 8
<212> TYPE: PRT
<213> ORGANISM: Rattus sp.

<400> SEQUENCE: 6
```

```
Lys Arg Leu Glu Thr Leu Leu Glu
1               5

<210> SEQ ID NO 7
<211> LENGTH: 9
<212> TYPE: PRT
<213> ORGANISM: Rattus sp.

<400> SEQUENCE: 7

Lys Arg Leu Glu Thr Leu Leu Glu Glu
1               5

<210> SEQ ID NO 8
<211> LENGTH: 4
<212> TYPE: PRT
<213> ORGANISM: Rattus sp.

<400> SEQUENCE: 8

Gln Lys Arg Leu
1

<210> SEQ ID NO 9
<211> LENGTH: 5
<212> TYPE: PRT
<213> ORGANISM: Rattus sp.

<400> SEQUENCE: 9

Gln Lys Arg Leu Glu
1               5

<210> SEQ ID NO 10
<211> LENGTH: 6
<212> TYPE: PRT
<213> ORGANISM: Rattus sp.

<400> SEQUENCE: 10

Gln Lys Arg Leu Glu Thr
1               5

<210> SEQ ID NO 11
<211> LENGTH: 7
<212> TYPE: PRT
<213> ORGANISM: Rattus sp.

<400> SEQUENCE: 11

Gln Lys Arg Leu Glu Thr Leu
1               5

<210> SEQ ID NO 12
<211> LENGTH: 8
<212> TYPE: PRT
<213> ORGANISM: Rattus sp.

<400> SEQUENCE: 12

Gln Lys Arg Leu Glu Thr Leu Leu
1               5

<210> SEQ ID NO 13
<211> LENGTH: 9
<212> TYPE: PRT
<213> ORGANISM: Rattus sp.

<400> SEQUENCE: 13

Gln Lys Arg Leu Glu Thr Leu Leu Glu
```

<210> SEQ ID NO 14
<211> LENGTH: 10
<212> TYPE: PRT
<213> ORGANISM: Rattus sp.

<400> SEQUENCE: 14

Gln Lys Arg Leu Glu Thr Leu Leu Glu Glu
1               5                   10

<210> SEQ ID NO 15
<211> LENGTH: 5
<212> TYPE: PRT
<213> ORGANISM: Rattus sp.

<400> SEQUENCE: 15

Ala Gln Lys Arg Leu
1               5

<210> SEQ ID NO 16
<211> LENGTH: 6
<212> TYPE: PRT
<213> ORGANISM: Rattus sp.

<400> SEQUENCE: 16

Ala Gln Lys Arg Leu Glu
1               5

<210> SEQ ID NO 17
<211> LENGTH: 7
<212> TYPE: PRT
<213> ORGANISM: Rattus sp.

<400> SEQUENCE: 17

Ala Gln Lys Arg Leu Glu Thr
1               5

<210> SEQ ID NO 18
<211> LENGTH: 8
<212> TYPE: PRT
<213> ORGANISM: Rattus sp.

<400> SEQUENCE: 18

Ala Gln Lys Arg Leu Glu Thr Leu
1               5

<210> SEQ ID NO 19
<211> LENGTH: 9
<212> TYPE: PRT
<213> ORGANISM: Rattus sp.

<400> SEQUENCE: 19

Ala Gln Lys Arg Leu Glu Thr Leu Leu
1               5

<210> SEQ ID NO 20
<211> LENGTH: 10
<212> TYPE: PRT
<213> ORGANISM: Rattus sp.

<400> SEQUENCE: 20

Ala Gln Lys Arg Leu Glu Thr Leu Leu Glu
1               5                   10

<210> SEQ ID NO 21
<211> LENGTH: 11
<212> TYPE: PRT
<213> ORGANISM: Rattus sp.

<400> SEQUENCE: 21

Ala Gln Lys Arg Leu Glu Thr Leu Leu Glu Glu
1               5                   10

<210> SEQ ID NO 22
<211> LENGTH: 6
<212> TYPE: PRT
<213> ORGANISM: Rattus sp.

<400> SEQUENCE: 22

Ala Ala Gln Lys Arg Leu
1               5

<210> SEQ ID NO 23
<211> LENGTH: 7
<212> TYPE: PRT
<213> ORGANISM: Rattus sp.

<400> SEQUENCE: 23

Ala Ala Gln Lys Arg Leu Glu
1               5

<210> SEQ ID NO 24
<211> LENGTH: 8
<212> TYPE: PRT
<213> ORGANISM: Rattus sp.

<400> SEQUENCE: 24

Ala Ala Gln Lys Arg Leu Glu Thr
1               5

<210> SEQ ID NO 25
<211> LENGTH: 9
<212> TYPE: PRT
<213> ORGANISM: Rattus sp.

<400> SEQUENCE: 25

Ala Ala Gln Lys Arg Leu Glu Thr Leu
1               5

<210> SEQ ID NO 26
<211> LENGTH: 10
<212> TYPE: PRT
<213> ORGANISM: Rattus sp.

<400> SEQUENCE: 26

Ala Ala Gln Lys Arg Leu Glu Thr Leu Leu
1               5                   10

<210> SEQ ID NO 27
<211> LENGTH: 11
<212> TYPE: PRT
<213> ORGANISM: Rattus sp.

<400> SEQUENCE: 27

Ala Ala Gln Lys Arg Leu Glu Thr Leu Leu Glu
1               5                   10

<210> SEQ ID NO 28

<211> LENGTH: 12
<212> TYPE: PRT
<213> ORGANISM: Rattus sp.

<400> SEQUENCE: 28

Ala Ala Gln Lys Arg Leu Glu Thr Leu Leu Glu Glu
1               5                   10

<210> SEQ ID NO 29
<211> LENGTH: 8
<212> TYPE: PRT
<213> ORGANISM: Mus musculus

<400> SEQUENCE: 29

Gly Tyr Ser Phe Thr Gly Tyr Tyr
1               5

<210> SEQ ID NO 30
<211> LENGTH: 8
<212> TYPE: PRT
<213> ORGANISM: Mus musculus

<400> SEQUENCE: 30

Ile Asn Pro Ser Thr Gly Gly Ala
1               5

<210> SEQ ID NO 31
<211> LENGTH: 8
<212> TYPE: PRT
<213> ORGANISM: Mus musculus

<400> SEQUENCE: 31

Ala Arg Leu Asp Ala Leu Asp Tyr
1               5

<210> SEQ ID NO 32
<211> LENGTH: 11
<212> TYPE: PRT
<213> ORGANISM: Mus musculus

<400> SEQUENCE: 32

Gln Ser Leu Val His Ser Asn Gly Asn Thr Tyr
1               5                   10

<210> SEQ ID NO 33
<211> LENGTH: 3
<212> TYPE: PRT
<213> ORGANISM: Mus musculus

<400> SEQUENCE: 33

Arg Val Ser
1

<210> SEQ ID NO 34
<211> LENGTH: 9
<212> TYPE: PRT
<213> ORGANISM: Mus musculus

<400> SEQUENCE: 34

Ser Gln Ser Thr His Val Pro Phe Thr
1               5

<210> SEQ ID NO 35
<211> LENGTH: 19
<212> TYPE: PRT

```
<213> ORGANISM: Mus musculus

<400> SEQUENCE: 35

Ser Gly Pro Val Leu Val Lys Pro Gly Ala Ser Val Lys Ile Ser Cys
1               5                   10                  15

Lys Ala Ser

<210> SEQ ID NO 36
<211> LENGTH: 17
<212> TYPE: PRT
<213> ORGANISM: Mus musculus

<400> SEQUENCE: 36

Met Phe Trp Val Lys Gln Ser Pro Glu Lys Ser Leu Glu Trp Ile Gly
1               5                   10                  15

Glu

<210> SEQ ID NO 37
<211> LENGTH: 38
<212> TYPE: PRT
<213> ORGANISM: Mus musculus

<400> SEQUENCE: 37

Thr Tyr Asn Leu Lys Phe Lys Ala Lys Ala Thr Leu Thr Val Asp Lys
1               5                   10                  15

Ser Ser Asn Thr Ala Tyr Met Gln Leu Lys Ser Leu Thr Ser Glu Asp
            20                  25                  30

Ser Ala Val Tyr Tyr Cys
        35

<210> SEQ ID NO 38
<211> LENGTH: 11
<212> TYPE: PRT
<213> ORGANISM: Mus musculus

<400> SEQUENCE: 38

Trp Gly Gln Gly Thr Ser Val Thr Val Ser Ser
1               5                   10

<210> SEQ ID NO 39
<211> LENGTH: 22
<212> TYPE: PRT
<213> ORGANISM: Mus musculus

<400> SEQUENCE: 39

Thr Gln Thr Pro Leu Ser Leu Pro Val Ser Leu Gly Asp Gln Ala Ser
1               5                   10                  15

Ile Ser Cys Arg Ser Ser
            20

<210> SEQ ID NO 40
<211> LENGTH: 17
<212> TYPE: PRT
<213> ORGANISM: Mus musculus

<400> SEQUENCE: 40

Leu His Trp Tyr Leu Gln Lys Pro Gly Gln Ser Pro Lys Leu Leu Ile
1               5                   10                  15

Tyr

<210> SEQ ID NO 41
```

```
<211> LENGTH: 36
<212> TYPE: PRT
<213> ORGANISM: Mus musculus

<400> SEQUENCE: 41

Asn Arg Phe Ser Gly Val Pro Asp Arg Phe Ser Gly Ser Arg Ser Gly
1               5                   10                  15

Thr Asp Phe Thr Leu Lys Ile Ser Arg Val Glu Ala Glu Asp Leu Gly
            20                  25                  30

Val Tyr Phe Cys
        35

<210> SEQ ID NO 42
<211> LENGTH: 10
<212> TYPE: PRT
<213> ORGANISM: Mus musculus

<400> SEQUENCE: 42

Phe Gly Ser Gly Thr Lys Leu Glu Ile Lys
1               5                   10

<210> SEQ ID NO 43
<211> LENGTH: 109
<212> TYPE: PRT
<213> ORGANISM: Mus musculus

<400> SEQUENCE: 43

Ser Gly Pro Val Leu Val Lys Pro Gly Ala Ser Val Lys Ile Ser Cys
1               5                   10                  15

Lys Ala Ser Gly Tyr Ser Phe Thr Gly Tyr Tyr Met Phe Trp Val Lys
            20                  25                  30

Gln Ser Pro Glu Lys Ser Leu Glu Trp Ile Gly Glu Ile Asn Pro Ser
        35                  40                  45

Thr Gly Gly Ala Thr Tyr Asn Leu Lys Phe Lys Ala Lys Ala Thr Leu
    50                  55                  60

Thr Val Asp Lys Ser Ser Asn Thr Ala Tyr Met Gln Leu Lys Ser Leu
65                  70                  75                  80

Thr Ser Glu Asp Ser Ala Val Tyr Tyr Cys Ala Arg Leu Asp Ala Leu
                85                  90                  95

Asp Tyr Trp Gly Gln Gly Thr Ser Val Thr Val Ser Ser
            100                 105

<210> SEQ ID NO 44
<211> LENGTH: 108
<212> TYPE: PRT
<213> ORGANISM: Mus musculus

<400> SEQUENCE: 44

Thr Gln Thr Pro Leu Ser Leu Pro Val Ser Leu Gly Asp Gln Ala Ser
1               5                   10                  15

Ile Ser Cys Arg Ser Ser Gln Ser Leu Val His Ser Asn Gly Asn Thr
            20                  25                  30

Tyr Leu His Trp Tyr Leu Gln Lys Pro Gly Gln Ser Pro Lys Leu Leu
        35                  40                  45

Ile Tyr Arg Val Ser Asn Arg Phe Ser Gly Val Pro Asp Arg Phe Ser
    50                  55                  60

Gly Ser Arg Ser Gly Thr Asp Phe Thr Leu Lys Ile Ser Arg Val Glu
65                  70                  75                  80

Ala Glu Asp Leu Gly Val Tyr Phe Cys Ser Gln Ser Thr His Val Pro
```

-continued

```
                    85                  90                  95
Phe Thr Phe Gly Ser Gly Thr Lys Leu Glu Ile Lys
                100                 105
```

ANTIBODY USEFUL IN NEUROLOGICAL OR NEURODEGENERATIVE DISORDERS

The present invention relates to the field of antibodies. In particular, it provides an anti-NMDA antibody or fragment or derivative thereof which is effective in inhibiting the deleterious effects of tissue-type plasminogen activator (t-PA) mediated by N-methyl-D-aspartate (NMDA) receptors being toxic to neurons and inflicting damage to the neurovascular unit/blood-brain barrier (BBB) or regulating it in a way that leads to pathological consequences. Also provided are medical uses, in particular for the treatment of neurological or neurodegenerative disorders, e.g. multiple sclerosis.

Multiple sclerosis (MS) is both an inflammatory and a degenerative disease of the central nervous system (CNS). It is characterised by infiltrating immune cells, loss of myelin due to oligodendrocytic cells death, and axonal damages.

The cause or causes of MS have not been definitively proven. MS is believed to be an immune-mediated disease in which the body's own immune system damages structures of the nervous system. Although its physiopathology is not well understood, results from animal models suggest that excitotoxic processes are involved in the pathology of MS (Pitt et al., 2000; Correa et al., 2007). Indeed, imbalanced glutamate homeostasis contributes to axonal and oligodendroglial pathology in human MS, suggesting that this imbalance could be manipulated with a therapeutic aim (Werner et al., 2001). For example, blockers of NMDA receptors, such as memantine, have been shown to attenuate white matter damage (Manning et al., 2008). A strong release of glutamate by leukocytes and glial cells, an altered glutamate metabolism or an altered glutamate uptake may constitute the main mechanisms leading to increased extracellular levels of glutamate. Apart from MS, glutamate excitotoxicity seems also to be involved in other demyelinating disorders, such as Devic disease or idiopathic transverse myelitis.

In addition to glutamate excitotoxicity, the involvement of serine proteases (such as t-PA) in MS has been suggested. Actually, t-PA may promote demyelination, because plasmin (which is generated by the action of t-PA on plasminogen) can directly degrade Myelin Basic Protein (MBP) (Cammer et al., 1978). Furthermore plasmin is the key initiator of the matrix metalloproteinase (MMP) activation cascade. MMP activity has been documented to have an important role in the breakdown of myelin membranes (Cuzner and Opdenakker, 1999). Interestingly, t-PA was also reported to promote excitotoxic neuronal cell death (Nicole et al., 2001) and to contribute to glutamate-induced oligodendrocyte injury (Pitt et al., 2000). Moreover, impaired t-PA-driven fibrinolysis may contribute to axonal damage in MS (East et al., 2005). Several groups suggest a relationship between t-PA and glutamatergic transmission (Nicole et al, 2001, Fernandez-Monreal et al., 2004; Samson et al., 2008, for review: Yepes et al., 2009). Of note, the various functions of t-PA in the body forbid an approach by which t-PA would be totally neutralised. This is indicated by the finding that t-PA$^{-/-}$ mice, after a delayed onset of symptomatic disease, exhibit increased severity and delayed recovery in the Experimental Autoimmune Encephalomyelitis (EAE) model of MS (Lu et al., 2002).

t-PA is a serine protease with two faces, which displays key roles in the intravascular space, at the interface between blood and brain and in the brain parenchyma (for review: Yepes et al., 2008). In the intravascular compartment, t-PA's main substrate is the inactive zymogen plasminogen and its main role is to promote fibrinolysis. Blood-derived t-PA can cross both the intact and the injured blood-brain barrier (Benchenane et al. 2005a, Benchenane et al., 2005b) and thus can, together with endogenously produced t-PA, interact in the brain parenchyma with a variety of substrates, thus extending its functions above t-PA/plasmin(ogen)-driven extracellular matrix degradation.

There is a growing body of evidence indicating that the interaction between t-PA and the N-methyl-D-aspartate receptor (NMDAR), the low density lipoprotein receptor-related protein (LRP), annexin-II in glial cells and/or neurons activates cell signalling processes, which can, when excessive, result in deleterious outcomes including cerebral oedema, hemorrhagic transformation and cell death. Based on these multiple pathophysiological effects of t-PA, the participation of endogenous t-PA (supported by the side effects of exogenously applied rt-PA) is discussed beyond the established role in ischemic disorders for several neurological or neurodegenerative disorders such as epilepsy, Alzheimer's disease, multiple sclerosis or meningitis.

Synaptic NMDA receptors may be distinguished from extrasynaptic NMDA receptors in the way that hypoactivity of synaptic NMDA receptors is harmful to neurons. Enhancing their activity triggers multiple neuroprotective pathways. Low levels of activation of extrasynaptic NMDARs have no effects on neuronal survival but increasing their activity has been reported to activate cell death pathways and exacerbate certain neuro-degenerative processes (Hardingham and Bading, 2010). Thus, means to effect a specific reduction of activity of extrasynaptic, sparing that of synaptic, NMDA receptors, would be a promising therapeutic aim in neurological diseases.

The formation of cerebral inflammatory infiltrates significantly contributes to the development of neuronal deficits in a number of brain disorders like MS (Zipp et al., 2006). Under physiological conditions the brain microvessel endothelium, in conjunction with attached glial cells and their extensions, acts as a blood-brain barrier (BBB) through its tight junction complexes, hereby limiting the entry of leukocytes.

Cerebral invasion of immune cells requires opening of the endothelial tight junctions and damage to the BBB is a hallmark of many neurological disorders. Knowledge of molecular and cellular processes at the BBB underlying cerebral inflammation may help in the development of novel therapeutic approaches aimed at preserving the BBB and modulating cellular influx. Interestingly, t-PA was also described to alter inflammatory reactions in the CNS by increasing the permeability of the blood-brain barrier (Paterson et al., 1987). Recent results indicate that t-PA facilitates monocyte induced BBB opening and subsequent monocyte traversal across the rat and human BBB in vitro (Reijerkerk et al., 2008).

The prevalence of MS is between 2 and 150 per 100,000. No cure is known for multiple sclerosis. The goals of MS therapy are mainly to restore function, to prevent MS attacks and to halt disability progression.

For symptomatic treatment in acute MS attacks, corticosteroids are routinely used. However they do not appear to have significant long-term effects. For disease-modifying treatment, dimethyl fumarate, fingolimod, glatiramer acetate, interferon-beta 1, mitoxantrone, natalizumab and teriflunomide are currently in use. Most of these drugs are only approved for the relapsing-remitting subtype of MS, in which they are somewhat effective at decreasing the number of attacks. Additionally, MK-801 (dizocilpine) has been reported to be neuroprotective and effective in a model of multiple sclerosis. However, MK-801 is a non-selective NMDA receptor-antagonist, which has unacceptable adverse effects.

Issues of medicaments currently used in MS include adverse effects and poor tolerability. The antibody currently used in multiple sclerosis, natalizumab, is a humanised monoclonal antibody recognising the cell adhesion molecule α4-integrin. After being linked with the neurological condition progressive multifocal leukoencephalopathy (PML), it had been transiently withdrawn from the US market. Other reported adverse effects of natalizumab include hepatotoxicity.

Antibodies against the NMDA receptor are known as such (see e.g. EP 2 289 542 A1), but specific epitopes or complementarity determining regions (CDRs) have not been disclosed.

Antibodies against the NMDA receptor are found in a certain autoimmune disease, anti-NMDA receptor encephalitis. These antibodies bind to the NR1 (also called GlunN1) subunit of the NMDA receptor, and their binding epitope has been delineated (Gleichman et al., 2012). Upon binding, these antibodies trigger similar effects as MK-801, but the effects are more severe. The antibodies trigger a quick stimulation of the NMDA receptors and their subsequent internalisation. Thus the NMDA receptors cannot be stimulated any longer, in particular the ones whose activation has a neuroprotective effect. Patients suffering from anti-NMDA receptor encephalitis present with acute anxiety, behavioural changes or psychosis and develop seizures or neuropsychological deficits. Within days or weeks, reduced consciousness, movement disorders, hypoventilation and autonomic imbalance appear, which often makes admission to intensive care units necessary.

Thus, there is a continuing need for novel, and preferably improved, means for the treatment of MS. It thus is the object of the present invention to provide a novel means for the treatment of a neurological or neurodegenerative disorder such as MS.

According to a first aspect of the present invention, this object is solved by an anti-NMDA receptor antibody or a fragment or derivative thereof, wherein said antibody, fragment or derivative (a) is capable of binding an epitope comprising an amino acid sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27 and 28, (b) comprises one or more complementarity determining regions having an amino acid sequence selected from the group consisting of SEQ ID NOs: 29, 30, 31, 32, 33 and 34, or (c) comprises one or more complementarity determining regions which have an amino acid sequence selected from the group consisting of SEQ ID NOs: 29, 30, 31, 32, 33 and 34 which is altered at one or two amino acid positions or which contains an insertion of one or more amino acids, and which are functional equivalents of the corresponding unaltered complementarity determining regions.

The above-mentioned epitope is in a region of the NR1 (also called GlunN1) subunit of the NMDA receptor that interacts with t-PA and is conserved between species. The present inventors have found that an antibody binding to this epitope or having the above-mentioned complementarity determining regions is able to inhibit the deleterious effects of tissue-type plasminogen activator (t-PA) mediated by the N-methyl-D-aspartate (NMDA) receptor. As described below, such antibody blocks the potentiation of lesions induced by t-PA, and also has an effect in the absence of exogenously administered t-PA, which means that it has an effect on endogenous t-PA. However, in the complete absence of t-PA, the antibody does not have any effect at all. It can be concluded that the antibody inhibits the interaction between the NMDA receptor and t-PA. Thereby the deleterious consequences associated with this interaction are mitigated or prevented. By this specific action at a circumscribed target, other functions of t-PA that are beneficial, such as its role in restoring vascular blood flow and rearranging the cellular matrix, remain unaffected.

Accordingly the antibody or fragment or derivative thereof according to the invention is useful as a means for the treatment of a neurological or neurodegenerative disorder such as MS.

The autoreactive antibodies in anti-NMDA receptor encephalitis bind to a region in the amino-terminal domain of the NR1 subunit that involves the region of residues 368 and 369 and a region from amino acid position 144 to 156, which regions are in close proximity in the folded domain (Gleichman et al., 2012).

The hazards of a strategy aiming to block the interaction of t-PA with the NMDA receptor are illustrated by these autoimmune antibodies, which share with t-PA the NR1 subunit as a target: An antibody might be prone to cause encephalitis if it interacted with, blocked or otherwise affected the binding epitopes of said injurious autoimmune antibodies. Nonetheless, the current inventors succeeded in developing an antibody avoiding this risk.

The present inventors have generated a monoclonal antibody according to the invention after immunisation with a fragment corresponding to amino acids 19 to 371 of the NR1 subunit. Although this fragment included the immunogenic regions recognised by the anti-NMDA receptor encephalitis antibodies, the inventors have found that the created antibody did not elicit the deleterious effect of the anti-NMDA receptor encephalitis antibodies. Moreover, the antibody according to the invention selectively blocked only certain functions of the NMDA receptor. The binding epitopes of the anti-NMDA receptor encephalitis antibodies and the antibody according to the invention do not overlap. The inventors have also found antibodies generated after immunisation with the 19-371 fragment that bound outside the epitope described in alternative (a) above and did not show the positive effects of the antibody according to the invention.

A preferred antibody according to the invention has a favourable efficacy profile. A particularly preferred antibody according to the invention has one or more of the following characteristics: it has an increased efficacy (e.g. regarding a prevention of MS attacks, an improvement or a restoration of function, a neuroprotective effect or a halt in disability progression), it is more convenient to use, needs to be administered less frequently or less regularly or has less adverse effects or an increased tolerability as compared to a previous MS medicament, it is a high-affinity antibody, has a low cross-reactivity, is safe, economical or usable in MS subtypes for which there is currently no adequate treatment.

The term "antibody" preferably refers to a protein comprising at least two heavy chains and two light chains connected by disulfide bonds. The term "antibody" includes naturally occurring antibodies as well as all recombinant forms of antibodies, e.g., antibodies expressed in prokaryotes, unglycosylated antibodies, humanised antibodies, and chimeric antibodies. Each heavy chain consists of a heavy chain variable region (VH) and a heavy chain constant region (CH). Each light chain consists of a light chain variable region (VL) and a light chain constant region (CL). The heavy chain-constant region comprises three or—in the case of antibodies of the IgM- or IgE-type—four heavy chain-constant domains (CH1, CH2, CH3 and CH4) wherein the first constant domain CH1 is adjacent to the variable region and may be connected to the second constant domain CH2 by a hinge region. The light chain-constant region consists only of one constant domain. The variable regions can be further subdivided into regions of hypervariability, termed complementarity determining regions (CDRs), interspersed with regions that are more conserved, termed framework regions (FR), wherein each variable region comprises three CDRs and four FRs. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" according to the invention, however, also includes unusual antibodies such as heavy chain antibodies, i.e. antibodies only composed of one or more, in particular two heavy chains, and nanobodies, i.e. antibodies only composed of a single monomeric variable domain.

As used herein, the term "protein" refers to a molecular chain of amino acids or a complex of more than one amino acid chain. A protein may contain any of the naturally occurring amino acids as well as artificial amino acids and may be of biologic or synthetic origin. A protein may be modified, naturally (post-translational modifications) or synthetically, by e.g. glycosylation, amidation, carboxylation and/or phosphorylation. A protein comprises at least two amino acids, but does not have to be of any specific length; this term does not include any size restrictions. In the present application, the terms "protein", "polypeptide" and "peptide" are used interchangeably. Preferably, a protein comprises at least 10 amino acids, preferably at least 50 amino acids, at least 100 amino acids and most preferred at least 100 amino acids.

A "fragment or derivative" of an antibody is preferably a protein or glycoprotein which is derived from said antibody and is capable of binding to the same antigen, in particular to the same epitope as the antibody. Thus, a fragment or derivative of an antibody herein generally refers to a functional fragment or derivative. In particularly preferred embodiments, the fragment or derivative of an antibody comprises a heavy chain variable region. It has been shown that the antigen-binding function of an antibody can be performed by fragments of a full-length antibody or derivatives thereof. Examples of fragments or derivatives of an antibody include (i) Fab fragments, monovalent fragments consisting of the variable region and the first constant domain of each the heavy and the light chain; (ii) F(ab)2 fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) (Fv)2 fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular. These antibody fragments and derivatives are obtained using conventional techniques known to those skilled in the art.

A target amino acid sequence is "derived" from a reference amino acid sequence, for example, if the target amino acid sequence shares a homology or identity over its entire length with a corresponding part of the reference amino acid sequence of 60% or more, preferably 70% or more, 75% or more, more preferably 80% or more, 85% or more, 90% or more, 93% or more, 95% or more, 97% or more, 98% or more, or 99% or more. For example, if a framework region of a humanised antibody is derived from a variable region of a particular human antibody, then the amino acid of the framework region of the humanised antibody shares a homology or identity over its entire length with the corresponding framework region of the human antibody of 60% or more, preferably 70% or more, 75% or more, more preferably 80% or more, 85% or more, 90% or more, 93% or more, 95% or more, 97% or more, 98% or more, or 99% or more. The "corresponding part" or "corresponding framework region" means that, for example, framework region 1 of a heavy chain variable region (FRH1) of a target antibody corresponds to framework region 1 of the heavy chain variable region of the reference antibody. The same is true, for example, for FRH2, FRH3, FRH4, FRL1, FRL2, FRL3 and FRL4. In particular embodiments, a target amino acid sequence which is "derived" from a reference amino acid sequence is 100% homologous, or in particular 100% identical, over its entire length with a corresponding part of the reference amino acid sequence.

Preferably an antibody or fragment or derivative thereof according to the invention has two heavy chain variable regions that are identical to each other and/or two light chain variable regions that are identical to each other.

The expression "comprise", as used herein, besides its literal meaning also includes and preferably refers to the expressions "consist essentially of" and "consist of", unless dictated otherwise by the context. Thus, the expression "comprise" refers to embodiments wherein the subject-matter which "comprises" specifically listed elements does not comprise further elements as well as embodiments wherein it may and/or indeed does encompass further elements. Likewise, the expression "have" is to be understood the same way as the expression "comprise".

As mentioned above, according to certain embodiments, the antibody or fragment or derivative thereof according to the invention comprises one or more complementarity determining regions having an amino acid sequence selected from the group consisting of SEQ ID NOs: 29, 30, 31, 32, 33 and 34, or functional equivalents thereof, which may in each case be altered at one or two amino acid positions or which may in each case contain an insertion of one or more amino acids (in particular an insertion of 1, 2, 3, 4, 5, 6, 7 or 8 amino acids, preferably such amino acids as determined by alignment with human CDRs sequences displaying a high homology with the CDRs of SEQ ID NOs: 29, 30, 31, 32, 33 and 34, wherein preferred insertions are between amino acids 4 and 5 of SEQ ID NO: 29, between amino acids 4 and 5 of SEQ ID NO: 30, between amino acids 4 and 5 of SEQ ID NO: 31, between amino acids 6 and 7 of SEQ ID NO: 32, between amino acids 2 and 3 of SEQ ID NO: 33 and/or between amino acids 5 and 6 of SEQ ID NO: 34).

The present invention encompasses embodiments in which the antibody, fragment or derivative comprises 1, 2, 3, 4, 5 or preferably 6 of the complementarity determining regions having an amino acid sequence selected from the group consisting of SEQ ID NOs: 29, 30, 31, 32, 33 and 34, or the functional equivalents thereof. In this context, SEQ ID NOs: 29, 30 and 31 preferably correspond to CDR1, CDR2 and CDR3 of a heavy chain, respectively, and SEQ ID NOs: 32, 33 and 34 preferably correspond to CDR1, CDR2 and CDR3 of a light chain, respectively.

The present invention also provides an antibody or a fragment or derivative thereof (preferably as described above), which is capable of binding to at least a portion of a region (preferably to the complete region) of an NMDA receptor that interacts with t-PA and wherein said binding inhibits (partially or fully, in particular with regard to the physiological consequences) the interaction between the NMDA receptor and t-PA, whereby at least one function of the NMDA receptor is selectively inhibited. This function is preferably a deleterious function of the NMDA receptor, more preferably one that is mediated or aggravated by t-PA. Since t-PA-NMDA receptor binding in certain contexts leads to undesirable consequences, in particular in multiple sclerosis, inhibition of such t-PA-NMDA receptor binding has a beneficial therapeutic effect. The selectivity of inhibition of the NMDA receptor results preferably from selectively inhibiting certain functions of the NMDA receptor (e.g. a neurotoxic calcium influx), or selectively inhibiting a certain subset of NMDA receptors (such as a subset mediating deleterious effects, e.g. a subset selected from the group consisting of synaptic and extrasynaptic NMDA receptors), preferably extrasynaptic NMDA receptors. Preferably binding of the antibody, fragment or derivative does not lead to the stimulation of the NMDA receptor, does not lead to an internalisation of the NMDA receptor and/or does not impair the normal function of the NMDA receptor. Preferably binding of the antibody, fragment or derivative does not elicit any encephalopathies, no behavioural effects or, generally spoken, no deleterious effect itself.

Preferably the NMDA receptor is the rat or the human NMDA receptor. Preferably t-PA is rat or human t-PA. Preferably the region of the NMDA receptor that interacts with t-PA is in the amino-terminal domain of the GluN1-1a subunit (in particular in amino acids 19 to 371 thereof) of the NMDA receptor.

Such antibody, fragment or derivative binds to only a small part of one of the NMDA subunits. This allows a specific intervention at the NMDA receptor, which does not interfere with the physiological function of the NMDA receptor, but only inhibits the t-PA-induced potentiation of the NMDA receptor activity.

Preferably the binding of the antibody or fragment or derivative thereof according to the invention prevents the cleavage of the extracellular domain of the NR1 subunit of the NMDA receptor.

Preferably the antibody or fragment or derivative thereof according to the invention is capable of specific binding (e.g. to the epitope or the region mentioned above). For example, this may decrease adverse effects or increase tolerability of the antibody, fragment or derivative.

"Specific binding" preferably means that an agent such as an antibody binds more strongly to a target such as an epitope for which it is specific as compared to the binding to another target. An agent binds more strongly to a first target as compared to a second target if it binds to the first target with a dissociation constant (Kd) that is lower than the dissociation constant for the second target. Preferably the dissociation constant for the target to which the agent binds specifically is more than 2-fold, preferably more than 5-fold, more preferably more than 10-fold, even more preferably more than 20-fold, 50-fold, 100-fold, 200-fold, 500-fold or 1000-fold lower than the dissociation constant for the target to which the agent does not bind specifically. Most preferably the agent does not bind at all to the second target to a relevant extent.

A preferred antibody according to the invention partially or completely blocks cell surface diffusion of neuronal extrasynaptic NMDA receptor, in particular t-PA-promoted cell surface diffusion of neuronal extrasynaptic NMDA receptor.

Preferably the antibody according to the invention (i) suppresses monocyte and/or T-cell migration across the blood brain barrier and/or (ii) stops spinal cord myelin damage and immune cell infiltration.

A preferred embodiment of the present invention is an antibody as described above, which is a monoclonal antibody, or a fragment or derivative thereof.

Preferably the antibody, fragment or derivative as described above has one or more of the following characteristics:

(a) it comprises a heavy chain framework region sharing a homology or identity of 80% or more with a framework region having an amino acid sequence selected from the group consisting of SEQ ID NOs: 35, 36, 37 and 38 and/or a light chain framework region sharing a homology or identity of 80% or more with a framework region having an amino acid sequence selected from the group consisting of SEQ ID NOs: 39, 40, 41 and 42, or (b) it shows cross-reactivity with an antibody produced by a deposited hybridoma selected from the group consisting of 15A4B2E5, 15A4B2F3, 15A4B2, 6C9A3, 6C9A3F4 and 6C9A3F6.

Herein, the designations of hybridomas have upper case letters (such as 15A4B2E5), and the designations of monoclonal antibodies produced by the hybridomas have lower case letters (such as 15a4b2e5).

Preferably, as described above for amino acid sequences derived from a reference amino acid sequence, the sequence homology or identity is 85% or more, 90% or more, 93% or more, 95% or more, 97% or more, 98% or more, 99% or more, or 100%.

In a preferred embodiment an above-mentioned percentage value of sequence homology or identity applies to the complete framework region of the heavy chain and/or the light chain. This means that for the heavy chain, the complete heavy chain variable region of the antibody, excluding the CDRs, is compared with joined SEQ ID NOs: 35, 36, 37 and 38, and for the light chain, the complete light chain variable region of the antibody, excluding the CDRs, is compared with joined SEQ ID NOs: 39, 40, 41 and 42.

In another preferred embodiment the antibody as described above comprises one or two heavy chain variable regions comprising the amino acid sequence of SEQ ID NO: 43 and/or comprises one or two light chain variable regions comprising the amino acid sequence of SEQ ID NO: 44. A preferred fragment or derivative thereof shows cross-reactivity with said antibody. Preferably an antibody or fragment or derivative thereof according to the invention has two such heavy chain variable regions and/or two such light chain variable regions.

A further preferred derivative has two heavy chain variable regions that are identical to each other and share a homology or identity of e.g. 80% or more over their entire length with a heavy chain variable region comprising the amino acid sequence of SEQ ID NO: 43 and/or has two light chain variable regions that are identical to each other and share a homology or identity of e.g. 80% or more over their entire length with a light chain variable region comprising the amino acid sequence of SEQ ID NO: 44.

Specific antibodies are produced by injecting an antigen into a mammal, such as a mouse, rat, rabbit, goat, sheep, or horse. Blood isolated from these animals contains polyclonal antibodies directed against said antigen in the serum. To obtain an antibody that is specific for a single epitope of an antigen, antibody-secreting lymphocytes are isolated from the animal and immortalised by fusing them with a cancer cell line, resulting in hybridoma cells. Single hybridoma cells are then isolated by dilution cloning to generate cell clones that all produce the same monoclonal antibody.

Furthermore, the antibody according to the invention is preferably a human, murine, goat, primate or camel antibody or is derived therefrom. It may be a chimeric or humanised antibody. It may be an antibody of any isotype or subclass thereof, in particular of the IgG, IgM, IgA, IgE or IgD isotype or a subclass thereof such as IgG1. Preferably, the fragment or derivative of the antibody according to the invention is selected from the group consisting of a Fab fragment, a F(ab)$_2$ fragment, a Fd fragment, a Fv fragment, a scFv fragment, a (Fv)$_2$ fragment, and a multibody. The antibody or fragment or derivative thereof may be a single chain construct comprising only one amino acid molecule, or a multi chain construct comprising more than one amino acid molecule which preferably are covalently connected to each other, for example by disulfide bonds.

In certain embodiments, the antibody or fragment or derivative thereof according to the invention is engineered in such a way that its heavy chain variable region (VH) contains at least one CDR which is derived from a different antibody than at least a part of the remaining VH. For example, the VH comprises at least one CDR, preferably two or three CDRs, derived from one antibody, for example a mouse, camel, goat or primate antibody, and at least one FR, preferably two, three or four FRs, derived from another antibody or group of antibodies, preferably antibodies of another species, in particular from human antibodies. In this embodiment, the antibody or fragment or derivative thereof may further comprise a light chain variable region (VL). In particular, the VL may be derived from the antibody from which the one or more CDRs of the VH are derived, or the VL may be a construct wherein one, two or three CDRs are derived from the same antibody as the one or more CDRs of the VH, while one, two, three or preferably all four FRs are derived from the same species, in particular the same antibody or group of antibodies as the one or more FRs of the VH. Moreover, the antibody or fragment or derivative thereof may further comprise one, two, three or four heavy chain constant regions (CH) and/or one light chain constant region (CL) which are preferably derived from the same species, in particular the same antibody or group of antibodies as the FRs of the variable regions. In preferred embodiments, the FRs of the variable regions and the constant regions are not derived from one specific antibody but have an amino acid sequence that represents a consensus sequence or another preferred sequence derived from a specific group of antibodies, for example a group of human antibodies.

In another embodiment, the antibody or fragment or derivative thereof according to the invention is chimeric and comprises one or more heavy chain and optionally light chain variable regions which are derived from one antibody and one or more heavy chain and optionally light chain constant regions which are derived from another antibody. Preferably, the two different antibodies are of different species, such as for example the variable regions are derived from a murine antibody while the constant regions are derived from a human antibody.

The antibody or fragment or derivative thereof according to the invention is preferably glycosylated. In preferred embodiments, it has a human glycosylation pattern which is also found on naturally occurring antibodies produced by the human body. Furthermore, the antibody or fragment or derivative thereof may comprise a glycosylation pattern that modulates, in particular enhances one or more activities thereof. For example, the glycosylation pattern may enhance the antibody's, fragment's or derivative's affinity towards its specific epitope, and/or its affinity towards its downstream receptors such as Fc receptors, in particular Fc gamma, Fc alpha or Fc epsilon receptors. Additionally or alternatively, the glycosylation pattern may enhance its complement dependent cytotoxicity (CDC) and/or its antibody-dependent cell-mediated cytotoxicity (ADCC). Finally, a special glycosylation pattern may be used to regulate the time of residence of the antibody in the body according to the medical need. To this end, the glycosylation pattern of the antibody or fragment or derivative thereof may be engineered or optimised, for example by using specific cell lines which are capable of producing the desired glycosylation pattern.

In certain embodiments, the engineered antibody or fragment or derivative thereof according to the invention is coupled to a further agent, forming a conjugate. The further agent is preferably useful in therapy, diagnosis, prognosis and/or monitoring of a disease, in particular multiple sclerosis. For example, the further agent may be selected from the group consisting of antibodies or fragments of antibodies, in particular those of different species and/or different specificity, enzymes, interaction domains, stabilising domains, signalling sequences, detectable labels, fluorescent dyes, toxins, catalytic antibodies, cytolytic components, immunomodulators, immunoeffectors, MHC class I or class II antigens, chelators for radioactive labelling, radioisotopes, liposomes, transmembrane domains, viruses, and cells. It may be covalently, in particular by fusion or chemical coupling, or non-covalently attached to the antibody or fragment or derivative thereof.

The term "conjugate" preferably means two or more compounds which are linked together so that at least some of the properties from each compound are retained in the conjugate. Linking may be achieved by a covalent or non-covalent bond. Preferably, the compounds of the conjugate are linked via a covalent bond. The different compounds of a conjugate may be directly bound to each other via one or more covalent bonds between atoms of the compounds. Alternatively, the compounds may be bound to each other via a linker molecule wherein the linker is covalently attached to atoms of the compounds. If the conjugate is composed of more than two compounds, then these compounds may, for example, be linked in a chain conformation, one compound attached to the next compound, or several compounds each may be attached to one central compound.

According to a second aspect, the problem underlying the present invention is solved by an antibody produced by a deposited hybridoma selected from the group consisting of 15A4B2E5, 15A4B2F3, 15A4B2, 6C9A3, 6C9A3F4 and 6C9A3F6 (particularly a monoclonal antibody selected from the group consisting of 15a4b2e5, 15a4b2f3, 15a4b2, 6c9a3, 6c9a3f4 and 6c9a3f6), or a fragment or derivative thereof, which shows cross-reactivity with said antibody.

In a third aspect of the present invention, a nucleic acid encoding the antibody or fragment or derivative thereof according to the invention is provided.

The term "nucleic acid" includes single-stranded and double-stranded nucleic acids and ribonucleic acids as well as deoxyribonucleic acids. It may comprise naturally occurring as well as synthetic nucleotides. A nucleic acid may be natural or synthetically modified, for example by methylation, 5'- and/or 3'-capping.

The nucleic acid sequence of the nucleic acid according to the invention may have any nucleotide sequence suitable for encoding the antibody or fragment or derivative thereof according to the invention. However, preferably the nucleic acid sequence is at least partially adapted to the specific codon usage of the host cell or organism in which the nucleic acid according to the invention is to be expressed. The nucleic acid according to the invention may be double-stranded or single-stranded DNA or RNA, preferably double-stranded DNA such as cDNA or single-stranded RNA such as mRNA. It may be one consecutive nucleic acid molecule or it may be composed of several nucleic acid molecules, each coding for a different part of the antibody or fragment or derivative thereof according to the invention.

If the antibody or fragment or derivative thereof according to the invention is a single chain construct, the nucleic acid according to the invention is preferably a single nucleic acid molecule containing a coding region which codes for the entire antibody or fragment or derivative thereof. If the antibody or fragment or derivative thereof according to the invention is composed of more than one amino acid chain, the nucleic acid according to the invention may, for example, be a single nucleic acid molecule containing several coding regions each coding for one of the amino acid chains of the antibody or fragment or derivative thereof, preferably separated by regulatory elements such as IRES elements in order to generate separate amino acid chains, or the nucleic acid according to the invention may be composed of several nucleic acid molecules wherein each nucleic acid molecule comprises one or more coding regions each coding for one of the amino acid chains of the antibody or fragment or derivative thereof. In addition to the coding regions encoding the antibody or fragment or derivative thereof according to the invention, the nucleic acid according to the invention may also comprise further nucleic acid sequences or other modifications which, for example, may code for other proteins, may influence the transcription and/or translation of the coding region(s), may influence the stability or other physical or chemical properties of the nucleic acid, or may have no function at all.

A fourth aspect of the present invention relates to an expression cassette or vector comprising the nucleic acid according to the invention and a promoter operatively connected with said nucleic acid.

The term "expression cassette" preferably refers to a nucleic acid construct which is capable of enabling and regulating the expression of a coding nucleic acid sequence introduced therein. An expression cassette may comprise promoters, ribosome binding sites, enhancers and other control elements which regulate transcription of a gene or translation of an mRNA. The exact structure of an expression cassette may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the operatively connected nucleic acid. Expression cassettes may also comprise enhancer sequences or upstream activator sequences.

According to the invention, the term "promoter" refers to a nucleic acid sequence that is located upstream (5') of the nucleic acid sequence that is to be expressed and controls expression of the sequence by providing a recognition and binding site for RNA polymerases. The "promoter" may include further recognition and binding sites for further factors which are involved in the regulation of transcription of a gene. A promoter may control the transcription of a prokaryotic or eukaryotic gene. Furthermore, a promoter may be "inducible", i.e. initiate transcription in response to an inducing agent, or may be "constitutive" if transcription is not controlled by an inducing agent. A gene that is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

The term "vector" is used herein in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes. The term "plasmid" as used herein generally relates to a construct of extrachromosomal genetic material, usually a circular DNA duplex, which can replicate independently of chromosomal DNA.

In addition to the nucleic acid according to the invention and the promoter, the expression cassette or vector according to the invention may comprise further elements, in particular elements which are capable of influencing and/or regulating the transcription and/or translation of the nucleic acid according to the invention, the amplification and/or reproduction of the expression cassette or vector, the integration of the expression cassette or vector into the genome of a host cell, and/or the copy number of the expression cassette or vector in a host cell. Suitable expression cassettes and vectors comprising respective expression cassettes for expressing antibodies are well known in the art and thus, need no further description here.

In a fifth aspect, the present invention relates to a host cell comprising the nucleic acid according to the invention or the expression cassette or vector according to the invention.

According to the invention, the term "host cell" relates to any cell that can be transformed or transfected with an exogenous nucleic acid. The term "host cells" comprises prokaryotic (e.g. *E. coli*) or eukaryotic cells (e.g. mammalian cells, in particular human cells, yeast cells and insect cells). Particular preference is given to mammalian cells such as cells from humans, mice, hamsters, pigs, goats, or primates. The cells may be derived from a multiplicity of tissue types and may comprise primary cells and cell lines. A nucleic acid may be present in the host cell in the form of a single copy or of two or more copies and, in one embodiment, is expressed in the host cell.

The host cell according to the invention may be any host cell. It may be an isolated cell or a cell contained in a tissue. Preferably, the host cell is a cultured cell, in particular a primary cell or a cell of an established cell line. Preferably, it is a bacterial cell such as *E. coli*, a yeast cell such as a *Saccharomyces* (in particular *S. cerevisiae*) cell, an insect cell such as a Sf9 cell, or a mammalian cell, in particular a human cell, a hamster cell such as a CHO cell, or a primate cell. In preferred embodiments, the host cell is optimised for expression of glycoproteins, in particular antibodies, having a specific glycosylation pattern. Preferably, the codon usage in the coding region of the nucleic acid according to the invention and/or the promoter and the further elements of the expression cassette or vector are compatible with and, more preferably, optimised for the type of host cell used. Preferably, the antibody or fragment or derivative thereof according to the invention is produced by a host cell or cell line as described above.

In a sixth aspect, the present invention also provides a composition (preferably a pharmaceutical composition) comprising the antibody or fragment or derivative thereof according to the invention, the nucleic acid according to the invention, the expression cassette or vector according to the invention or the host cell according to the invention, and optionally one or more components selected from the group consisting of carriers, solvents, diluents, and excipients, such as a buffer, preservative or tonicity modifier.

The composition may also contain more than one of each of the mentioned components. In a preferred pharmaceutical composition according to the invention all components are pharmaceutically acceptable. The composition may be a solid or fluid composition, in particular a—preferably aqueous—solution, emulsion or suspension or a lyophilised powder.

The term "pharmaceutical composition" particularly refers to a composition suitable for administering to a patient, i.e., a composition containing components that are pharmaceutically acceptable.

The term "patient" means, according to the invention, a human being, a nonhuman primate or another animal, in particular a mammal such as a cow, horse, pig, sheep, goat, dog, cat or a rodent such as a mouse and rat. In a particularly preferred embodiment, the patient is a human being.

In a seventh aspect, the invention provides the antibody or fragment or derivative thereof according to the invention, the nucleic acid according to the invention, the expression cassette or vector according to the invention, the host cell according to the invention, or the (preferably pharmaceutical) composition according to the invention for use in medicine.

In an eighth aspect, the invention provides the antibody or fragment or derivative thereof according to the invention, the nucleic acid according to the invention, the expression cassette or vector according to the invention, the host cell according to the invention, or the (preferably pharmaceutical) composition according to the invention for use in the treatment, prognosis, diagnosis and/or monitoring of a neurological or neurodegenerative disorder or as a neuroprotectant.

The term "treatment" refers to any medical measure for preventing, reducing, mitigating or curing physiological disorders within a patient in need thereof.

The term "neurological disorder" as used herein is defined as disease, disorder or condition which directly or indirectly affects the normal functioning or anatomy of a subject's nervous system.

In the context of the invention the term "neurodegenerative disorder" is defined as disease in which cells of the central or peripheral nervous system are affected or lost.

Preferably, the neurological or neurodegenerative disorder is selected form the group consisting of multiple sclerosis, thrombotic disorder, stroke, TIA, intracerebral bleedings (including haemorrhagic stroke), epilepsy, temporal lobe epilepsy (TLE), amyotrophic lateral sclerosis, brain tumours, Parkinson disease, Alzheimer's disease, brain oedema, CNS complication resulting from parasitic, bacterial, fungal or viral infections, meningitis and encephalitis. A particularly preferred neurological or neurodegenerative disorder is multiple sclerosis.

Examples for neurological and/or neurodegenerative disorders are also traumatic brain injury, spinal cord injury, intracranial lesions or intravertebral lesions including, but not limited to, contusion, penetration, shear, compression or laceration lesions of the spinal cord or whiplash shaken infant syndrome.

In the context of the present invention the neurological disorders also include ischemic events, or ischemia or ischemic disorders which can be defined as any local or regional state of hypoxia in cells or tissues which are usually due to an inadequate blood supply (circulation), e.g. caused by a blockage or obstruction of a blood vessel in this area.

The hypoxia can cause acute or chronic injury as in hypoxia and/or ischemia including, but not limited to, cerebrovascular insufficiency, cerebral ischemia or cerebral infarction (including cerebral ischemia or infarctions originating from embolic occlusion and thrombosis), retinal ischemia (diabetic or otherwise, such as by acute vascular occlusion, in particular damage of the optic nerve after acute vascular occlusion), glaucoma (in particular damage of the optic nerve in glaucoma), retinal degeneration, multiple sclerosis, ischemic optic neuropathy, reperfusion following acute cerebral ischemia, perinatal hypoxic-ischemic injury, or intracranial hemorrhage of any type (including, but not limited to, epidural, subdural, subarachnoid or intracerebral hemorrhage).

Accordingly the term "ischemic disorder" encompasses thrombotic disorders which include conditions associated with or resulting from thrombosis or a tendency towards thrombosis. These conditions include conditions associated with arterial or venous thrombosis that can be treated with a thrombolytic drug.

The present invention also relates to a method of treatment of a neurological or neurodegenerative disorder by administering to a patient in need thereof a therapeutically effect amount of the antibody or fragment or derivative thereof according to the invention, the nucleic acid according to the invention, the expression cassette or vector according to the invention, the host cell according to the invention, or the (preferably pharmaceutical) composition according to the invention.

A "therapeutically effective amount" is defined as the amount of active ingredient that will reduce the symptoms associated with a neurological or neurodegenerative disease, such as multiple sclerosis. "Therapeutically effective" also refers to any improvement in disorder severity or the frequency of incidences compared to no treatment.

For use as detection agent in diagnosis, prognosis and/or monitoring of a disease, the antibody or fragment or derivative thereof according to the invention is preferably coupled to a labelling agent which is capable of producing a detectable signal. In particular, said labelling agent may be a radionuclide, a fluorophore or an enzyme.

In an further aspect, the present invention provides the antibody or fragment or derivative thereof according to the invention, the nucleic acid according to the invention, the expression cassette or vector according to the invention, the host cell according to the invention, or the (preferably pharmaceutical) composition according to the invention for use as a first agent in a combination therapy (preferably of a neurological or neurodegenerative disorder as defined above, in particular multiple sclerosis) together with a second agent for the treatment of a neurological or neurodegenerative disorder, wherein the second agent may alternatively be a neuroprotectant.

The first and the second agent may be present in a single composition or may be administered in two different compositions simultaneously or sequentially.

Lane 1 corresponds to purified antibody 15a4b2, lane 2 corresponds to purified antibody 15a4b2e5 and lane 3 corresponds to the supernatant obtained from hybridoma 15A4B2E5.

It can be seen that the antibodies recognise peptides "110" to "113".

Further details are described in Example 4.

Figure 2:
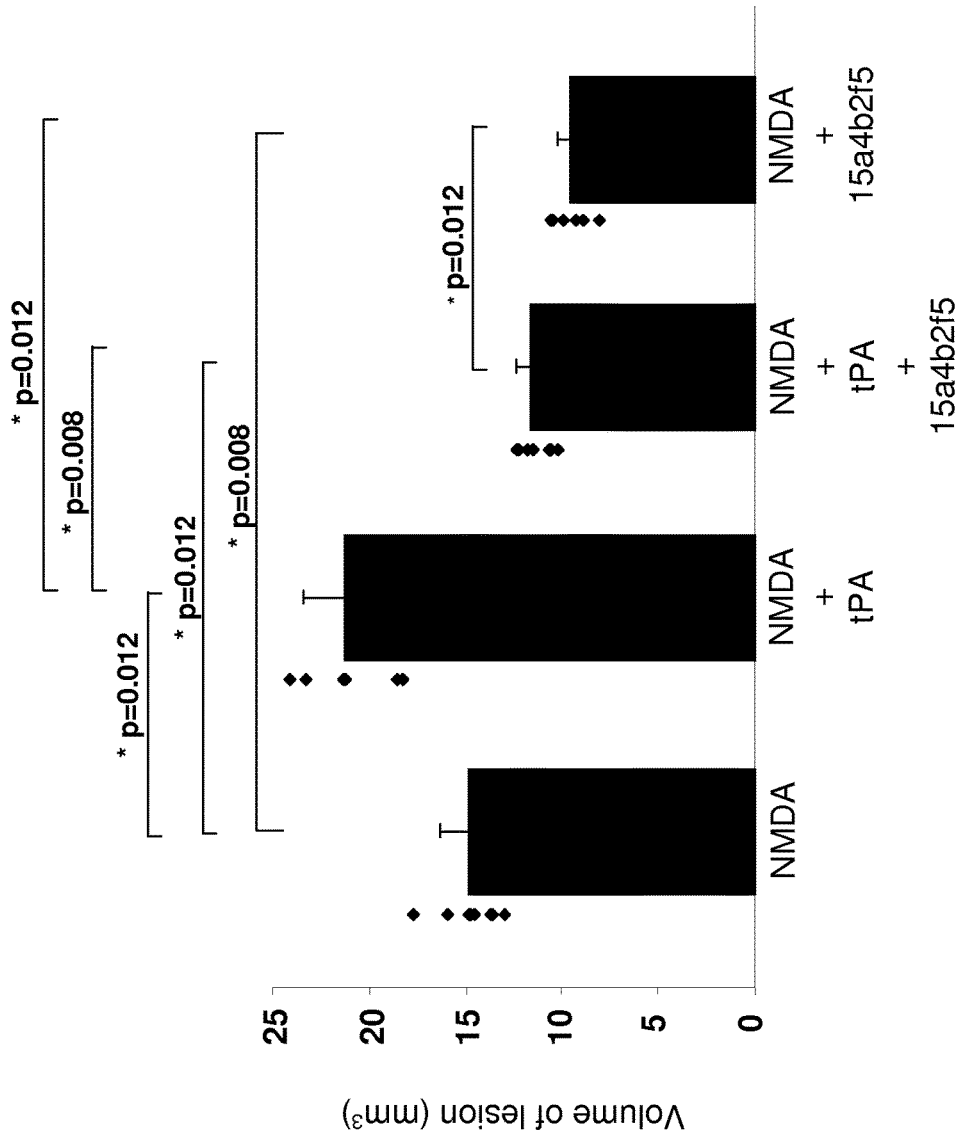

FIG. 2 shows the results of in vivo neurotoxicity assays performed with NMDA+/−t-PA+/− monoclonal antibody 15a4b2e5, as described in Example 5.

It can be seen that monoclonal antibody 15a4b2e5 blocks the potentiation of NMDA neurotoxicity by t-PA and also NMDA neurotoxicity in the absence of exogenous t-PA.

Figure 3:
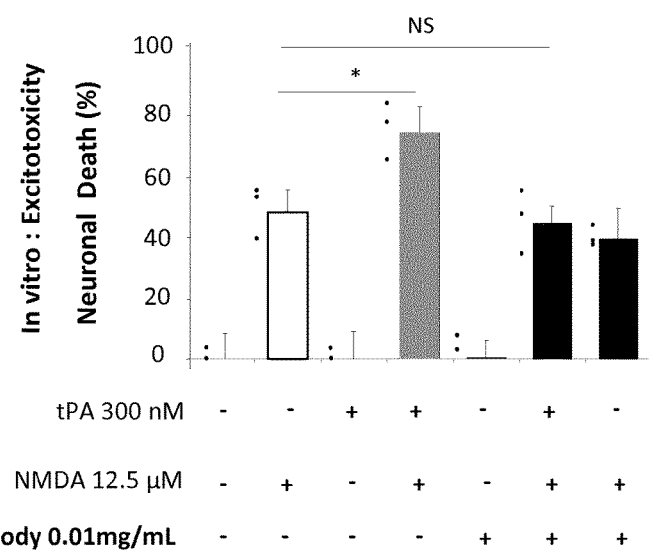
Figure 3:
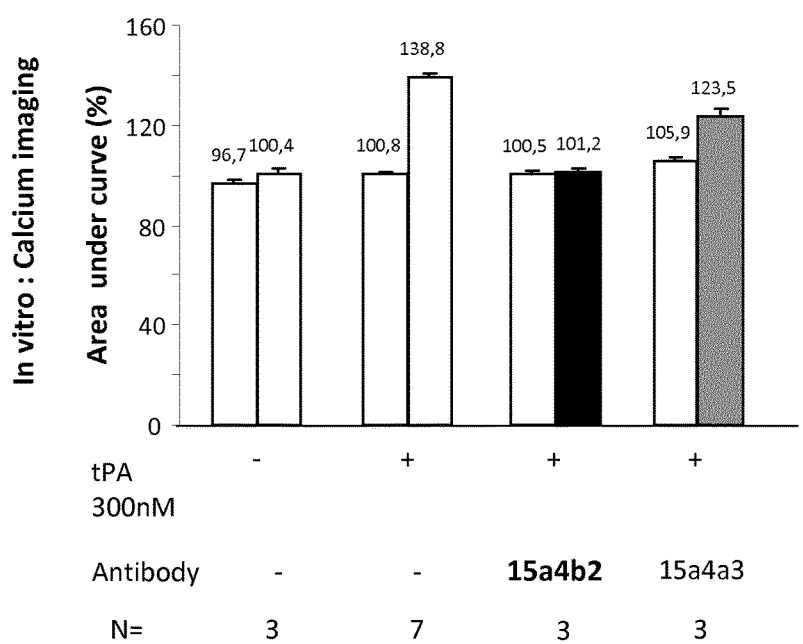

FIG. 3 shows that monoclonal antibody 15a4b2e5 blocks t-PA effects in cell culture, as described in Example 6.

Monoclonal antibody 15a4b2e5 prevents t-PA-promoted NMDA receptor signalling in vitro, without modification of the basal activity of the receptors.

The top panel shows effects on neuronal death. The bottom panel shows effects on calcium influx.

Figure 4:
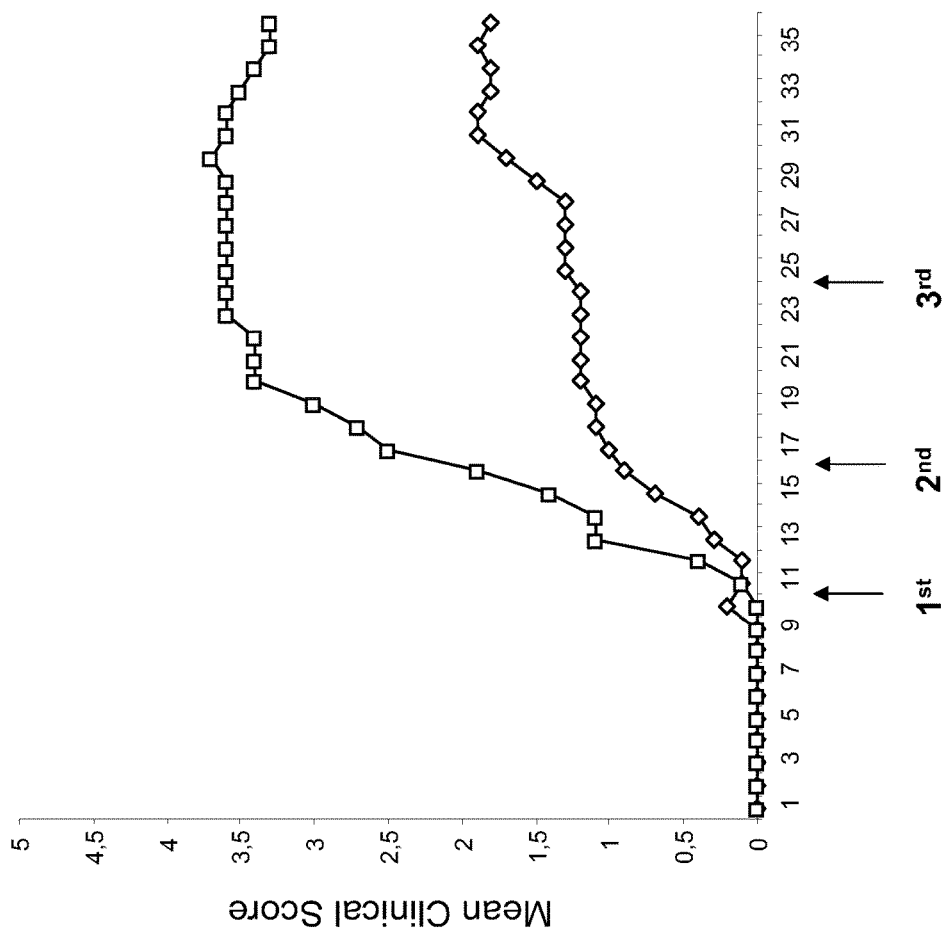

FIG. 4 shows that the monoclonal antibody 15a4b2e5 causes a large reduction of the clinical score in Experimental Autoimmune Encephalitis (EAE) in mice, as described in Example 7.

Figure 5:
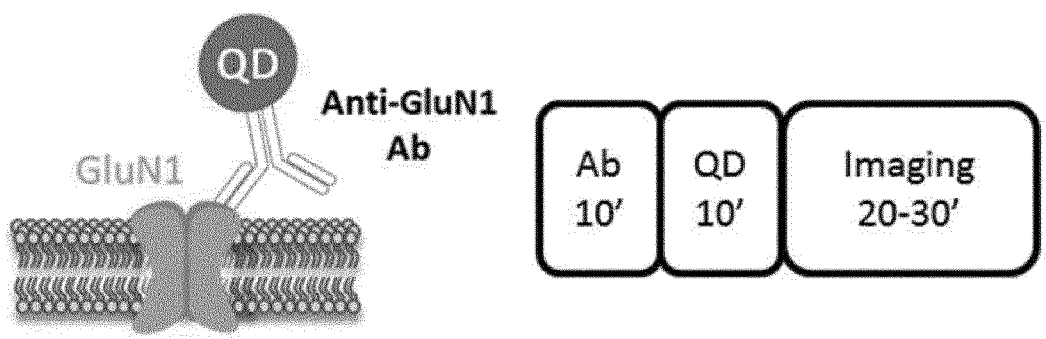
Figure 5:
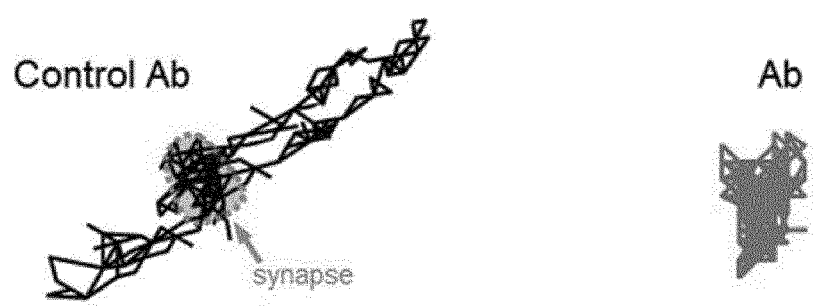

FIG. 5 shows that the monoclonal antibody 15a4b2e5 leads to a blockage of the diffusion of extrasynaptic NMDA receptors as described in Example 8.

Figure 6:
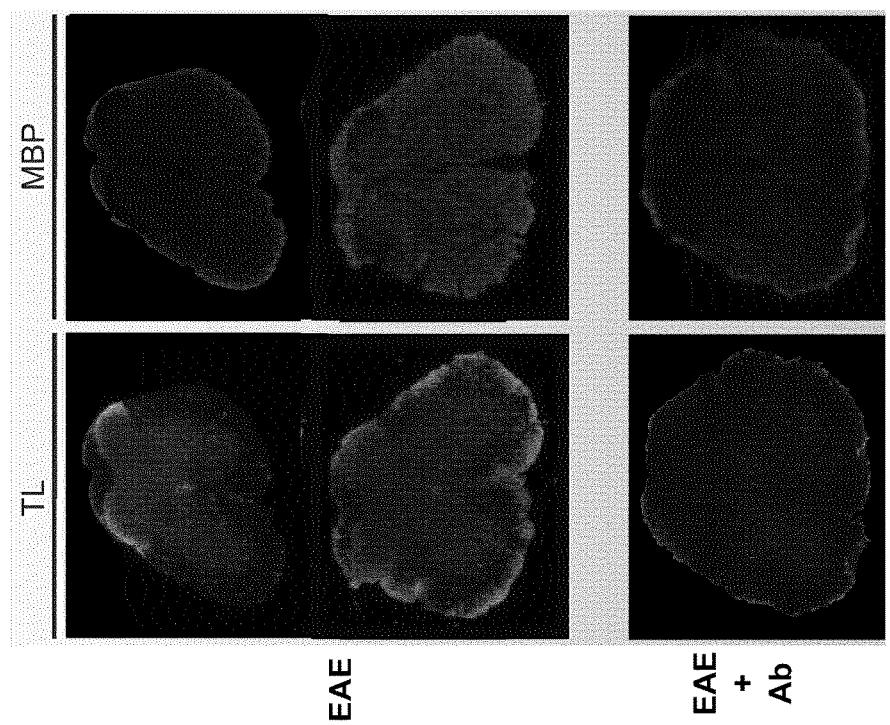
Figure 7:
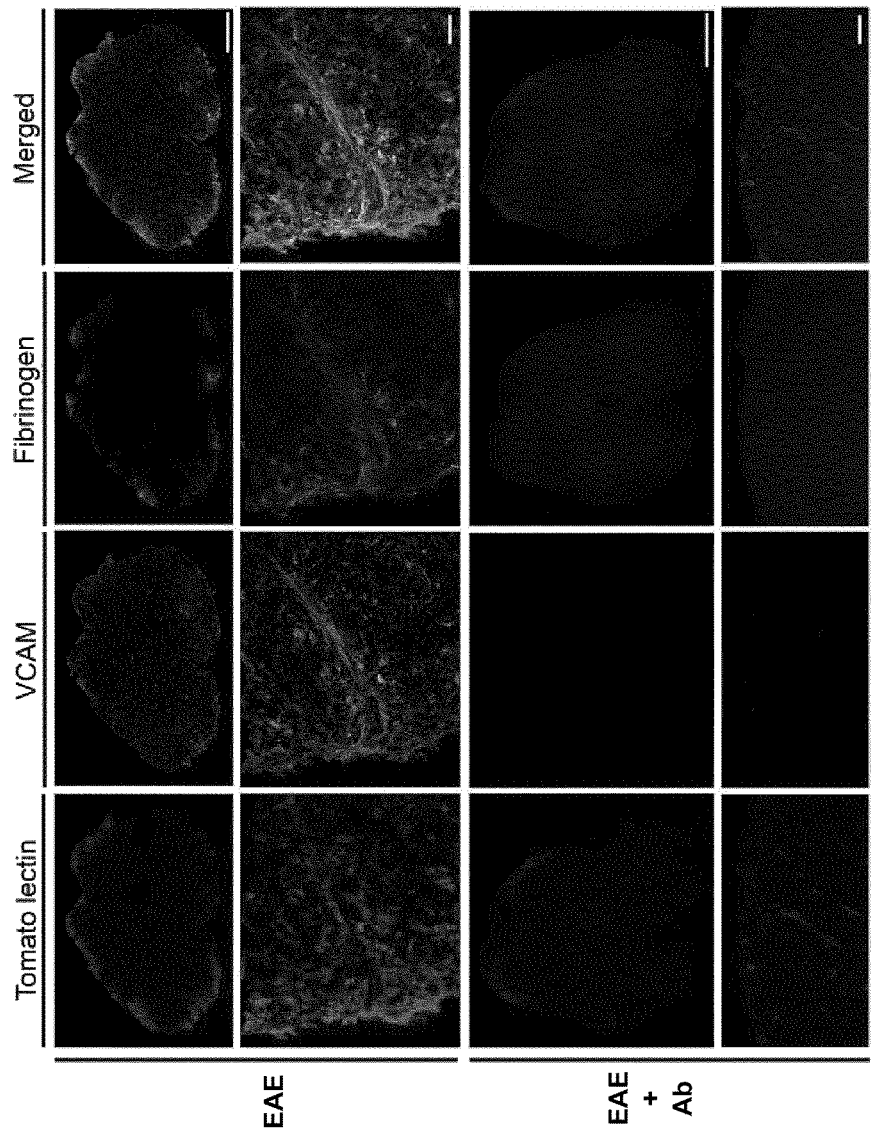
Figure 8:
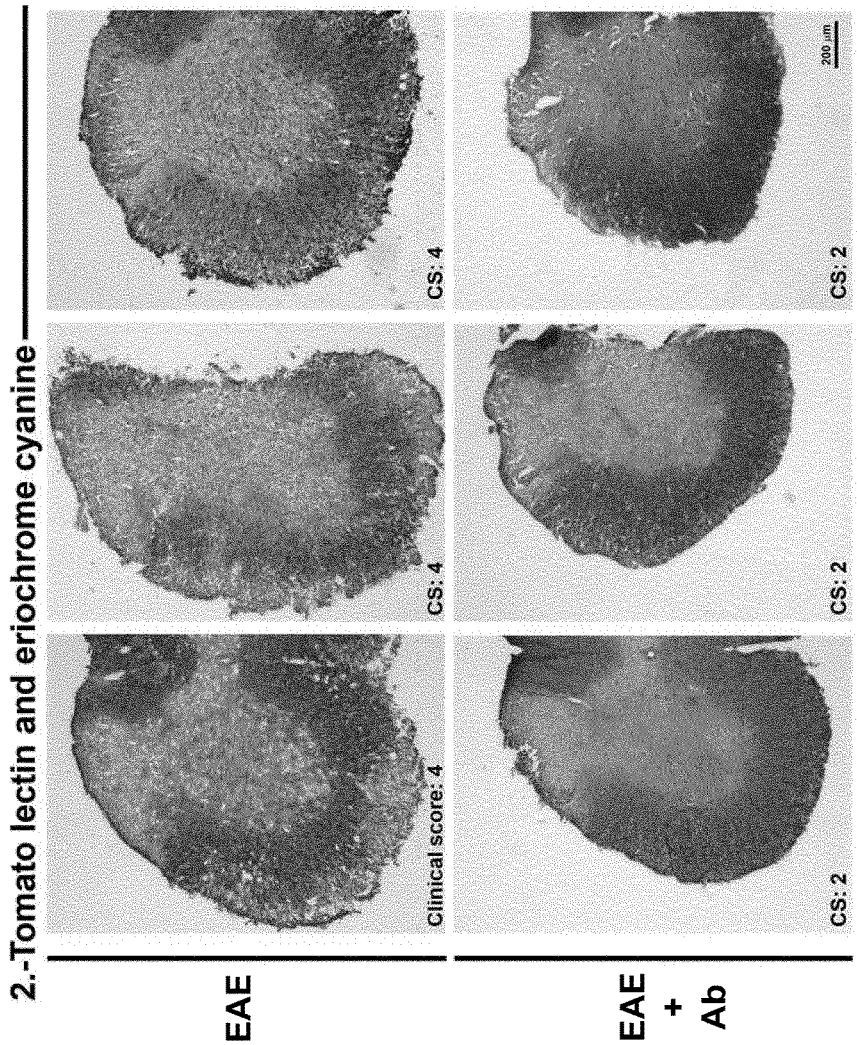

FIGS. 6, 7 and 8 show thoracic portions of EAE model mice stained for demyelination, cell infiltration and inflammation with and without treatment with antibody 15a4b2e5, as described in Example 9.

Figure 9:
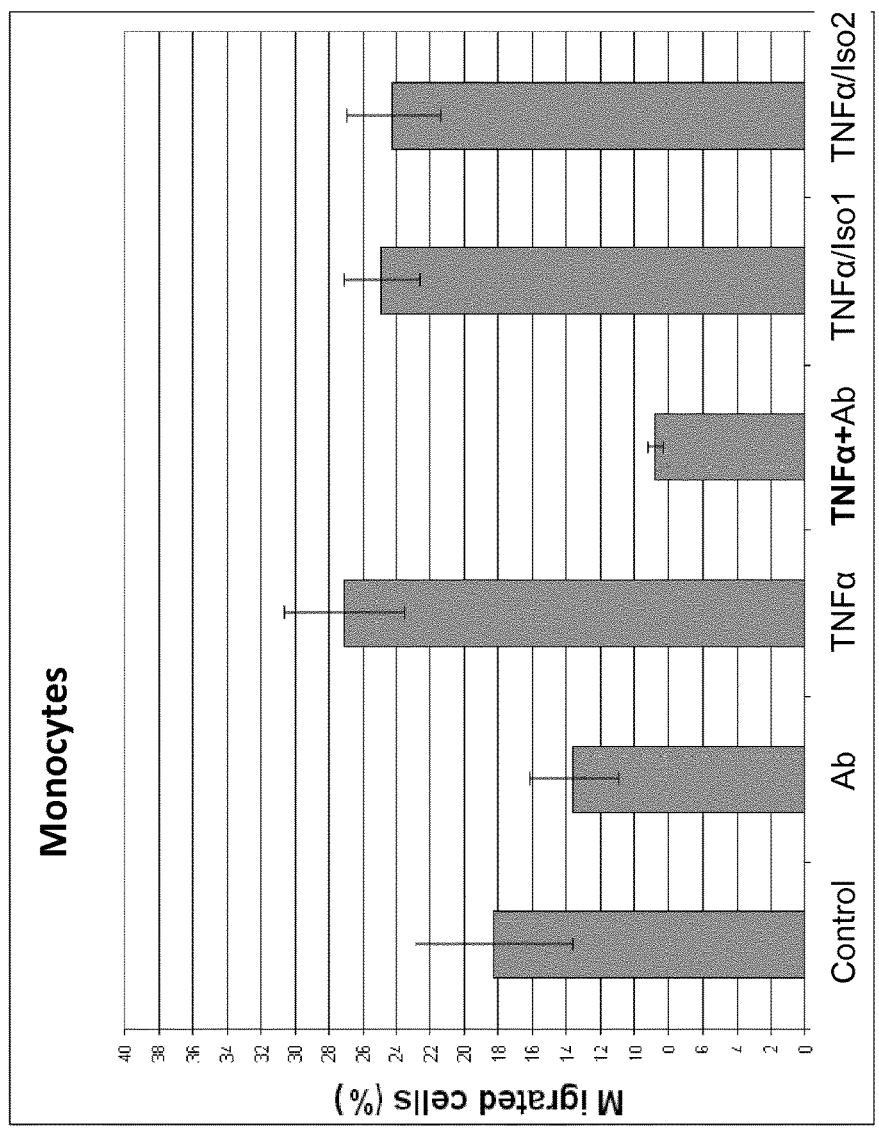
Figure 10:
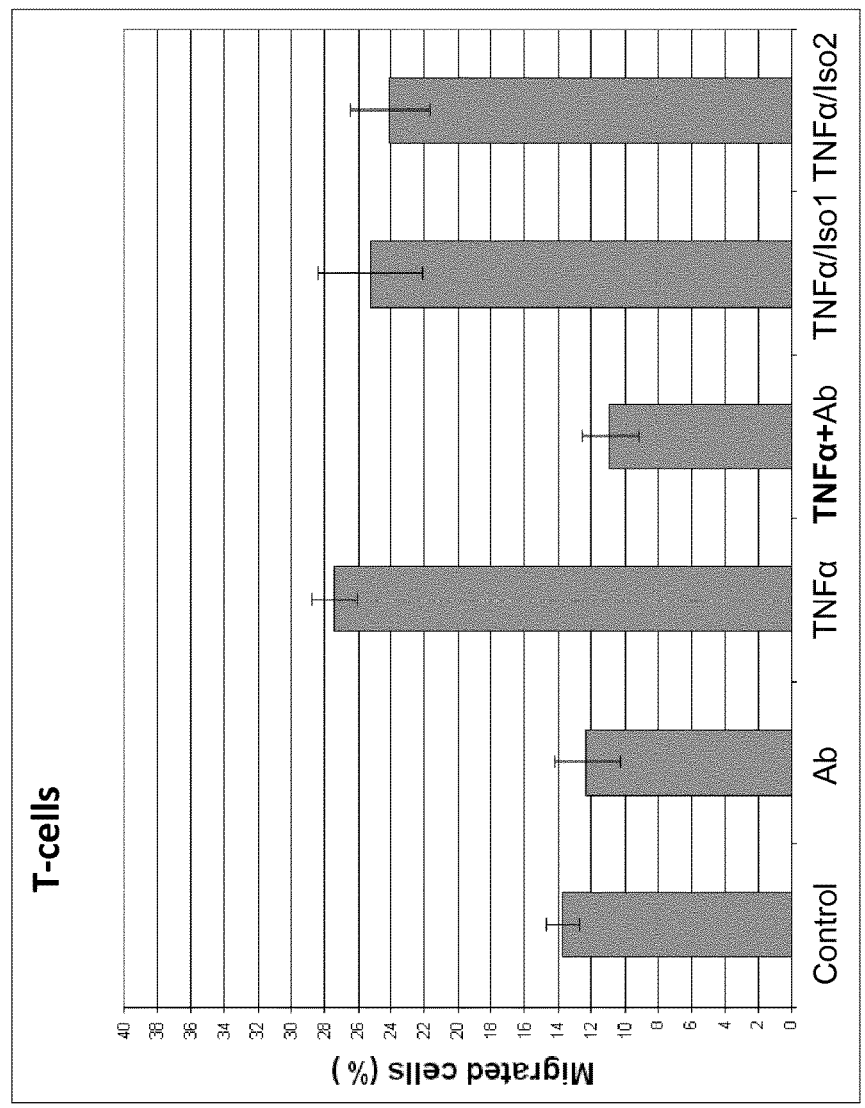

FIGS. 9 and 10 show the results of testing antibody 15a4b2e5 for its effects of transmigration of monocytes and T-lymphocytes across a model of the blood brain barrier, as described in Example 10.

EXAMPLES

Example 1: Generation of the Hybridomas 15A4B2E5 15A4B2F3, 15A4B2, 6C9A3, 6C9A3F4 and 6C9A3F6 and the Monoclonal Antibodies 15a4b2e5, 15a4b2f3, 15a4b2, 6c9a3, 6c9a3f4 and 6c9a3f6

A polyhistidine-tagged amino-terminal domain of the NR1-1a (GluN1-1a) subunit (rATD-NR1, amino acids 19 to 371 (a sequence absent from other glutamate receptor subunits and corresponding to the domain of interaction with t-PA) of the rat NMDA receptor was recombinantly produced as described by Benchenane et al. (2007). The region of the NR1-1a subunit encoding amino acids 19-371 corresponding to the NTD was amplified from the full-length rat NR1-1a cDNA, as described previously (Fernandez-Monreal et al., 2004). Recombinant proteins were purified from inclusion bodies of isopropyl 1-thio-D-galactopyranoside-induced bacterial cultures (*Escherichia coli*, M15 strain) on a nickel affinity matrix as described by the manufacturer (Qiagen, Courtaboeuf, France).

The product was used as an immunogen for BALB/C mice in order to generate a mouse polyclonal antibody.

Three mice per target were immunised. Each mouse received three injections and one last boost with the immunogen before fusion; two different adjuvants, RIBI and Alum were used.

Bleed testing was performed at day 25 and day 40 post immunisation in order to select mouse candidates for fusion by determining antibody titre by indirect ELISA. Splenocytes were isolated from selected mice.

Hybridoma cells were created by automated fusion with SP2/O-Ag14 myeloma cells on a TeMo Tecan Robot. After fusion, cells were seeded and cultured on 20 96-well plates in an automatic step with the TeMo Tecan Robot. Hybridoma cells were cultured under the standard selective medium containing azaserine as a selective compound. Evaluation of hybridoma growth and determination of the fusion rate was done under microscopic examination.

High throughput primary screening has been done by indirect ELISA, using the recombinant form of the rat amino-terminal domain of GluN1 as a bait.

Screening of IgG- and IgM-secreting clones was done on the following antigens: immunogen, negative polyhistidine-tagged protein, NMDA receptor positive cell membrane and control NMDA receptor negative cell membrane.

After primary screening by ELISA, 94 clones presented positive signals; among the 94 clones selected, 2 positive clones were further confirmed by indirect ELISA. These 2 clones were frozen (1 vial each) and sub-cloned by standard limiting dilution to generate the 15A4B5 and 6C9A3 sub-clones. These 2 sub-clones were frozen (2 vials/clone) and sub-cloned again to generate the sub-clones 15A4B2E5 and 15A4B2F3 as well as 6C9A3F4 and 6C9A3F6. These final sub-clones were frozen (5 vials each).

Functional tests on neurons were performed as follows:
(a) In Vitro Excitotoxicity Rapidly triggered excitotoxicity was induced, alone or in combination with rt-PA (20 µg/ml) and/or αATD-GluN1 or control Igs (0.01 mg/ml), by exposing neurons to 50 µmol/l NMDA for 1 hour and transferring cells back to serum-free medium. Neuronal death was quantified 24 hours later by lactate dehydrogenase release (Roche).

(b) Calcium Videomicroscopy

NMDA-evoked calcium influx in cultured cortical neurons was recorded as described earlier (Nicole et al., 2001). In detail, cell cultures were loaded with fura-2 (30 min, room temperature) in 5 µM fura-2/am plus 0.1% pluronic F-127 (Molecular Probes, Leiden, the Netherlands) and incubated for an additional 30 min period in a HEPES-buffered saline solution. Experiments were performed at room temperature, on the stage of a Nikon Eclipse inverted microscope equipped with a 75 W Xenon lamp and a Nikon 40×, 1.3 numerical aperture epifluorescence oil immersion objective. Fura-2 (excitation: 340, 380 nm, emission: 510 nm) ratio images were acquired with a CCD camera (Princeton Instrument, Trenton, N.J.), and digitized (256×512 pixels) using Metafluor 4.11 software (Universal Imaging Corporation, Chester, Pa.). Neurons were treated either with NMDA (50 µmol/l) alone or following a 30 minutes treatment in the presence of rt-PA (20 µg/ml) and/or αATD-GLuN1 or control Igs (0.01 mg/ml).

Example 2: Characteristics of Hybridomas 15A4B2E5, 15A4B2F3, 15A4B2, 6C9A3, 6C9A3F4 and 6C9A3F6

The hybridomas 15A4B2E5, 15A4B2F3, 15A4B2, 6C9A3, 6C9A3F4 and 6C9A3F6 (see Example 1) were deposited at the DSMZ (Leibniz-Institut DSMZ-Deutsche Sammlung von Mikroorganismen and Zellkulturen GmbH, Inhoffenstraße 7B, 38124 Braunschweig, Germany) and have been given the accession numbers DSM ACC3203 (received on May 29, 2013), DSM ACC3217 (received on Sep. 25, 2013), DSM ACC3216 (received on Sep. 25, 2013), DSM ACC3214 (received on Sep. 25, 2013), DSM ACC3200 (received on May 29, 2013) and DSM ACC3215 (received on Sep. 25, 2013), respectively. The depositors are PAION Deutschland GmbH, Martinstraße 10-12, D-52062 Aachen, Germany and INSERM, 101 rue de Tolbiac, F-75013 Paris, France, acting through its unit INSERM-UCBN, UMR-S U919, GIP CYCERON, Boulevard Henri Becquerel, BP 5229-14074 Caen Cedex, France.

All of these hybridomas produce antibodies of the isotype IgG2 (kappa light chains).

Suitable culturing conditions are as follows.

Culture medium: DMEM (4.5 g/l with Glutamine & sodium pyruvate) ref PAA E15-843 supplemented with 10% FCS; culture in incubator 37° C., 5 to 10% $CO_2$; thaw cells in water bath at 37° C. for few seconds and transfer ice cube into the 30 ml pre-heated medium (37° C.); after centrifugation (7 min, 1200 rpm) resuspend cells in 10 ml pre-heated culture medium (37° C.) and transfer in T25 $cm^2$ flask; put the flask horizontally in the incubator; split cells 1:5 Monday and Wednesday; 1:10 Friday.

Gentamycin 0.1 mg/ml may be used.

Example 3: Determination of the Sequence of the Variable Regions of the Heavy and Light Chains of the Monoclonal Antibody 15a4b2e5

1. mRNA Extraction and Reverse Transcription.

The 15A4B2E5 clone was used.

Total RNA was extracted from hybridoma in triplicate (A, B, C) with RNAble® reagent from cells in the exponential phase.

The samples were treated with DNAse 1 to remove all traces of genomic DNA. The cDNAs were synthesized from 2 µl RNA treated with DNAse 1 in a final volume of 40 µl (volume necessary for the realization of different PCR amplifications) from oligo-d(T) to reverse transcribe all strands of mRNA. A sample treated under the same conditions but without reverse transcriptase (RT) served as controls in the PCR to verify the absence of genomic DNA.

2. PCR Amplification of cDNA A, B, C.

The VH and VL gene segments of 15a4b2e5 were amplified by PCR using amplification conditions (T ° C. hybridization cycles) described by Lefranc and Lefranc, 1997.

The amplification products were visualized on a 1% agarose gel (Life Technologies, ref: AM9046, lot 1205021) containing 0.1% GelRed™ (INTERCHIM, ref: 41003, lot 12G0509) after deposition samples: 5 µl PCR/well products. 100 bp marker (Life Technologies, ref: 15628-019, lot 954661) and marker quantification Low DNA Mass™ Ladder (Life Technologies, ref: 10068-013, lot 1169490) 0.5 µg/well.

3. Sequencing

The sequences of the amplification products were determined by standard techniques.

Example 4: Mapping of the Binding Epitope of Monoclonal Antibodies 15a4b2e5 and 15a4b2

1. Overlapping peptides having a length of 15 amino acids covering the entire sequence of the immunogen of Example 1 were spot synthesised. The spot membrane was incubated with purified monoclonal antibodies 15a4b2 and 15a4b2e5 (1 µg/ml each) and with the supernatant obtained from hybridoma 15A4B2E5.

Figure 1:
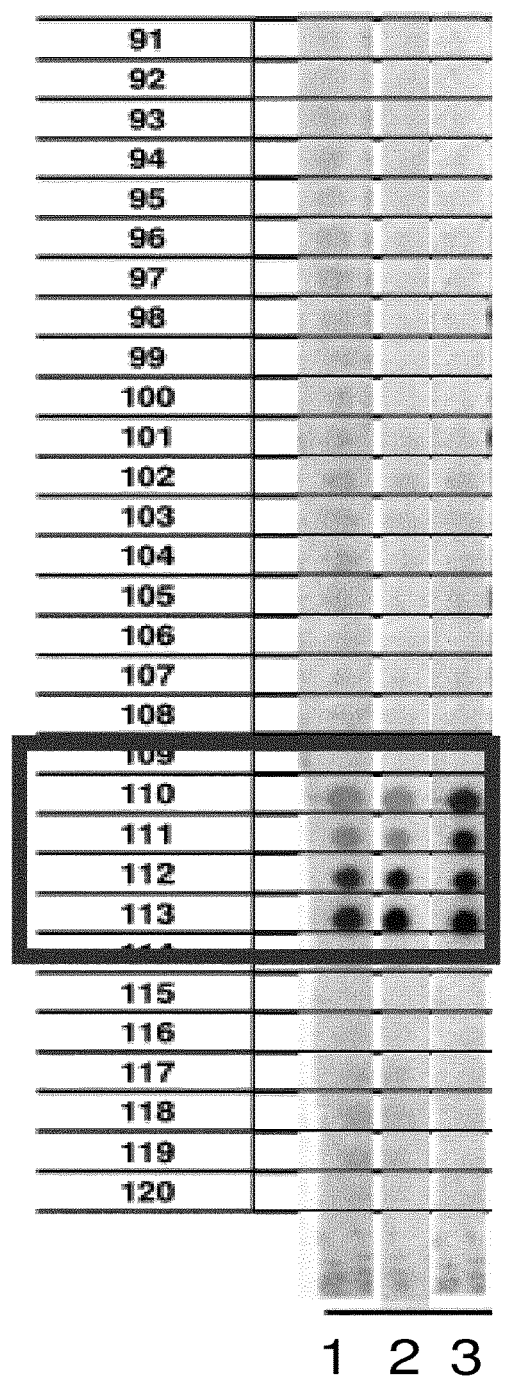
FIG. 1 shows the results obtained after mapping the binding epitope of monoclonal antibodies 15a4b2e5 and 15a4b2 with overlapping peptides of 15 amino acids each, from the rat NR1-1a subunit.

A set of peptides (15 amino acids each) overlapping the full sequence of the rat amino-terminal domain of GluN1 (amino acids 19 to 371) with an offset of three amino acids were used for an immunoblot assay. R The results are depicted in FIG. 1.

Lane 1 corresponds to purified antibody 15a4b2, lane 2 corresponds to purified antibody 15a4b2e5 and lane 3 corresponds to the supernatant obtained from hybridoma 15A4B2E5.

Only the data for peptides 91 to 120 are shown. Peptides not shown in FIG. 1 produced only background signals. The following table gives the sequences of peptides 91 to 120:

| | |
|---|---|
| 91 | YTAGFYRIPVLGLTT |
| 92 | GFYRIPVLGLTTRMS |
| 93 | RIPVLGLTTRMSIYS |
| 94 | VLGLTTRMSIYSDKS |
| 95 | LTTRMSIYSDKSIHL |
| 96 | RMSIYSDKSIHLSFL |
| 97 | IYSDKSIHLSFLRTV |
| 98 | DKSIHLSFLRTVPPY |
| 99 | IHLSFLRTVPPYSHQ |
| 100 | SFLRTVPPYSHQSSV |
| 101 | RTVPPYSHQSSVWFE |
| 102 | PPYSHQSSVWFEMMR |
| 103 | SHQSSVWFEMMRVYN |
| 104 | SSVWFEMMRVYNWNH |
| 105 | WFEMMRVYNWNHIIL |
| 106 | MMRVYNWNHIILLVS |
| 107 | VYNWNHIILLVSDDH |
| 108 | WNHIILLVSDDHEGR |
| 109 | IILLVSDDHEGRAAQ |
| 110 | LVSDDHEGRAAQKRL |
| 111 | DDHEGRAAQKRLETL |
| 112 | EGRAAQKRLETLLEE |
| 113 | AAQKRLETLLEERES |
| 114 | KRLETLLEERESKAE |

-continued

| | |
|---|---|
| 115 | ETLLEERESKAEKVL |
| 116 | LEERESKAEKVLQFD |
| 117 | RESKAEKVLQFDPGT |
| 118 | KAEKVLQFDPGTKNV |
| 119 | KVLQFDPGTKNVTAL |
| 120 | QFDPGTKNVTALLME |

The spots seen in FIG. 1 show that the tested antibodies recognise peptides 110 to 113, whereas peptides 91 to 109 and peptides 114 to 120 produced only background signals.

2. A similar experiment was repeated including the most reactive peptide identified in 1, either as wild type or containing a single point mutation for each of its amino acids alternatively.

This experiment confirmed the results obtained in 1. above.

An epitope mapping experiment as described in 1. above was also performed with supernatants from hybridomas 6C9A3F4 and 6C9A3. The results were comparable.

Example 5: Suppression of NMDA Neurotoxicity by Monoclonal Antibody 15a4b2e5

Excitotoxic lesions were performed under isoflurane-induced anesthesia in male swiss mice (25-30 g; CURB, Caen, France). Striatal injections (coordinates: 0.5 mm posterior, +2.0 mm lateral, -3.0 mm ventral to the bregma) of 10 nmol NMDA were performed after placing the animals under a stereotaxic frame. At the same time, t-PA (10 mg/kg) was injected intravenously either alone or in combination with antibody 15a4b2e5 (160 µg). Control IgGs from a negative clone were used as a control. After 24 h, brains were collected, frozen in isopentane, cryostat-cutted (20 µm sections), stained with thionine and analyzed.

The results are shown in FIG. 2.

The volume of lesions is depicted as bars (Bar 1: NMDA alone, Bar 2: NMDA+t-PA, Bar 3: NMDA+t-PA+monoclonal antibody 15a4b2e5, Bar 4: NMDA+monoclonal antibody 15a4b2e5).

Bar 1 shows the NMDA-induced neurotoxicity. Bar 2 shows NMDA-induced neurotoxicity boosted by t-PA. Bar 3 shows antibody suppression of the boost of NMDA-induced neurotoxicity. Bar 4 shows antibody inhibition of NMDA-induced neurotoxicity (antagonism of endogenous t-PA).

A comparison of the size of the bars shows the following:

Bar 1 vs Bar 2: t-PA enhances the neurotoxicity of NMDA.

Bar 2 vs Bar 3: monoclonal antibody 15a4b2e5 blocks the noxious effect of t-PA

Bar 1 vs Bar 3 and Bar 1 vs Bar 4: the effect of the antibody goes beyond blocking the damage by t-PA; it also reduces the noxious effect of NMDA, explained by antagonism of endogenous t-PA. Monoclonal antibody 15a4b2e5 thus blocks the potentiation of lesions induced by t-PA and is also beneficial in the absence of exogenous t-PA. This shows that e.g. the antibodies of the present invention have potential as a stand-alone drug.

Antibodies produced by the 6C9A3 family of hybridomas showed similar effects.

Example 6: Blockade of t-PA Effects by Monoclonal Antibody 15a4b2e5 in Cell Culture The results are depicted in FIG. 3.

FIG. 3A (top panel of FIG. 3) shows an assessment of excitotoxicity. Primary cultures of mouse cortical neurons (E16), maintained 12-14 days in vitro as previously described (Nicole et al., 2001) were studied. Complete neuronal death was defined by killing all neurons using Triton X100 exposure. All results were normalised to Triton X100.

Neuronal death was measured after in vitro administration of NMDA, t-PA and monoclonal antibody 15a4b2e5 in the mentioned combinations. The concentrations used were as follows: t-PA 300 nM, NMDA 12.5 µM, antibody 0.01 mg/ml.

From left to right, the bars show the following: control (no cell death), cell death caused by NMDA, lack of effect of t-PA, t-PA boost of NMDA-induced cell death, lack of effect of antibody alone, antibody suppression of boost of NMDA-induced cell death and lack of antibody influence on NMDA-induced cell death (no t-PA).

In the absence of NMDA, neither t-PA nor the antibody had any effect on neuronal death. The administration of NMDA caused neuronal death. This effect was potentiated when NMDA was administered in combination with t-PA. Additional administration of the antibody decreased neuronal death to the level seen with NMDA alone, indicating that the antibody blocked the interaction between t-PA and the NMDA receptor, but not the actual NMDA effect. This was confirmed by the finding that the administration of NMDA together with the antibody in the absence of t-PA caused neuronal death to the same extent as the administration of NMDA alone. This shows that the effect of the antibody depends on t-PA. In sum, the antibody suppressed the ability of t-PA to enhance NMDA-induced cell death, but did not influence the effect of NMDA alone FIG. 3B (bottom panel of FIG. 3) shows the results obtained by in vitro video calcium imaging. The concentration of t-PA was 300 nM. In each case, 100 to 150 cells were examined; the area under the curve of the calcium response was recorded and normalised to NMDA exposure (50 µM) alone.

The figure shows four pairs of bars. In each pair, the left bar corresponds to the addition of NMDA alone (control) and the right bar corresponds to the further addition of t-PA and/or the indicated antibody (second, third and fourth pair) or a repetition of the measurement of NMDA alone (first pair).

Thus, the four pairs of bars from left to right show the following: NMDA control, t-PA boost of NMDA, blockade of t-PA boost by effective antibody and lack of blockade of t-PA boost by ineffective antibody.

t-PA significantly increased NMDA-induced Ca2+ influx in cortical neurons. This effect was prevented by co-applying an effective antibody. One effective and one ineffective clone are illustrated in FIG. 3B.

Antibodies produced by the 6C9A3 family of hybridomas showed similar effects.

Example 7: Effects of Monoclonal Antibody 15a4b2e5 in an EAE Mouse Model

Mice were immunised subcutaneously with 200 µg of MOG35-55 peptide in CFA (Sigma) containing 4 µg of *M. tuberculosis* (H37Ra, Difco). Control animals received PBS instead of MOG peptide. All animals received 250 ng of pertussis toxin (Sigma) intravenously by injection in the tail vein at the time of immunisation and 48 hours later.

Animals were given monoclonal antibody 15a4b2e5 or an unrelated control IgG at 160 μg i.v after onset of symptoms. The effects of this treatment were assessed by the mean clinical score curve in sham and treated animals as previously described (Liu et al., 1998) and MRI was performed at different stages. All animal experimentation was carried out in accordance with European regulations.

Mice were examined daily for clinical signs of EAE and were scored as followed ("Clinical Score"): 0, no disease; 1, limp tail; 2, hindlimb weakness; 3, complete hindlimb paralysis; 4, hindlimb paralysis plus forelimb paralysis; and 5, moribund or dead.

The results are shown in FIG. 4.

The squares in the upper curve indicate the results of control mice (injection of unrelated control IgG). The diamonds in the lower curve indicate the results obtained with antibody 15a4b2e5.

It is apparent that monoclonal antibody 15a4b2e5 drastically and persistently reduced the mean clinical score from the time of its first injection.

The mean clinical score in the control group rose steeply after 10 days until it reached a value of about 3.5. In contrast, the mean clinical score in the 15a4b2e5 treatment group only increased mildly and never exceeded a value of around 2 (hindlimb weakness), even after 36 days (12 days after the third injection, when monitoring ended).

Mice received 160 μg of either monoclonal antibody 15a4b2e5 or a non-related control IgG per injection. The number of injections per mouse was 3. "$1^{st}$", "$2^{nd}$" and "$3^{rd}$" show the time points at which the injections were performed.

No indications of encephalitis were found in the antibody 15a4b2e5 treatment group.

The benefit observed was achieved with only three single injections, and notably already the first injection had a considerable effect. The three injections were arbitrarily placed along the time course of the disease, so that they may have been more than needed.

In a different setting, namely in a model of acute ischemic stroke, just a single injection was required for benefit.

Example 8: Antibody 15a4b2e5 Blocks t-PA-Promoted Neuronal Extrasynaptic NMDA Receptor Diffusion It is known that the autoantibodies found in the autoimmune disease anti-NMDA receptor encephalitis lead to a blockage of the diffusion of synaptic NMDA receptor (Mikasova et al., 2012).

In this example, the NMDA receptor distribution after administration of antibodies according to the invention was examined by single particle tracking and surface diffusion calculation, essentially as described in Mikasova et al., 2012. FIG. 5, upper right panel shows the following steps: Hippocampal primary neurons were incubated with the antibody for 10 min at 37° C. ("Ab 10'"), washed and incubated for 10 min at 37° C. with quantum dot-labelled secondary antibodies ("QD 10'"). This led to the surface labelling of GluN1 subunits. Quantum dots were monitored on randomly selected dendritic regions for 20 to 30 min ("Imaging 20-30'") and their trajectories were analysed.

FIG. 5, upper left panel is a schematic representation of the surface labelling of an NR1 (=GluN1) subunit of the NMDA receptor, using a single anti-NR1 antibody ("anti-GluN1 Ab") quantum dot ("QD") complex. The lower panel shows representative trajectories of a labelled NMDA receptor as tracked with either a control antibody ("Control Ab"; anti-Nter-NR1, from Alomone labs (AGC-001)) or with antibody 15a4b2e5 ("Ab"). It can be seen that the control antibody (which targets the N-terminal end of the NR1 (GluN1) subunit, but not its t-PA binding site fails to affect NMDA receptor membrane diffusion, which comprises both synaptic (circled with a green dotted line) and extrasynaptic trajectories. In contrast, antibody 15a4b2e5 ("Ab") leads to a selective blockage of the diffusion of extrasynaptic NMDA receptors, as indicated by the lack of extrasynaptic trajectories. Without being bound by theory, it is assumed that the neuroprotective effect of the antibodies according to the invention is related to their ability to prevent t-PA-promoted diffusion of extrasynaptic NMDA receptors, which are known to have neurotoxic effects.

Example 9: Antibody 15a4b2e5 Stops Myelin Damage

EAE model mice were treated with antibody 15a4b2e5 and myelin damage was investigated in the spinal cord.

FIGS. 6 to 8 show images of the thoracic portion of the spinal cord of EAE mice. It can be seen that antibody 15a4b2e5 stops myelin damage. The details are as follows:

FIG. 6 shows that Myelin Basic Protein ("MBP"), a protein from the myelin layer, which is used as a marker of demyelination, is detected in EAE ("EAE"), but to a much lesser extent with antibody 15a4b2e5 ("EAE+Ab"). Corresponding results are shown for T lymphocytes ("TL"), which are prominent in EAE ("EAE"), but virtually absent with antibody 15a4b2e5 ("EAE+Ab").

FIG. 7 shows infiltrated microglia cells (detected with tomato lectin), VCAM (Vascular Cell Adhesion Protein, an inflammation marker, which is correlated with increasing loss of function in the mouse EAE model), and fibrinogen (an inflammation marker) in EAE mice ("EAE"). Inflammation markers were suppressed in 15a4b2e5-treated EAE mice ("EAE+Ab").

FIG. 8 shows several areas with infiltrated cells (tomato lectin, marker of microglia cells; brown) and demyelination (detected with the myelin marker, eriochrome cyanine; blue) in EAE animals ("EAE"). There were no demyelinated areas or infiltrates in antibody-treated EAE mice ("EAE+Ab").

Example 10: Antibody 15a4b2e5 Suppresses Monocyte Migration and T-Cell Migration Across the Blood Brain Barrier Antibody 15a4b2e5 was tested in an in vitro model of the blood brain barrier (hCMEC/D3 were seeded at confluency onto collagen-coated Costar Transwell filter (pore-size 0.4 μm; Corning Incorporated) in growth medium containing 2.5% FCS and grown for 4 days) for its influence on TNFα-stimulated transmigration of monocytes and T-cells.

The results are shown in FIG. 9 (monocytes) and FIG. 10 (T-cells). Antibody 15a4b2e5 suppressed TNFα-stimulated transmigration of both monocytes and T-cells across the blood brain barrier ("TNFα+Ab"). In contrast, control immunoglobulins ("TNFα/Iso1", "TNFα/Iso2") did not suppress TNFα-stimulated transmigration.

REFERENCES CITED IN THE APPLICATION

Benchenane et al., 2005a, Circulation 111(17): 2241-2249
Benchenane et al., 2005b, Stroke 36(5): 1065-1070
Benchenane et al., 2007, J Cell Sci 120(Pt 4): 578-585.

Cammer et al., 1978, Proc Natl Acad Sci USA 75(3): 1554-1558
Correa et al., 2007, Neuroimmunomodulation 14(3-4): 182-187
Cuzner and Opdenakker, 1999, J Neuroimmunol 94(1-2): 1-14
East et al., 2005, Am J Pathol 167(2): 545-554
Fernandez-Monreal et al., 2004, J Biol Chem 279: 50850-50856
Gleichman et al., 2012, J Neurosci 32(32): 11082-11094
Hardingham and Bading, 2010, Nat Rev Neurosci 11: 682-696
Lu et al., 2002, J Neurosci 22(24): 10781-10789
Manning et al., 2008, J Neurosci 28(26): 6670-6678
Mikasova et al., 2012, Brain 135(5): 1606-1621
Paterson et al., 1987, Fed Proc 46(1): 91-96
Pitt et al., 2000, Nat Med 6(1): 67-70
Reijerkerk et al., 2008, J Immunol 181(5): 3567-3574
Samson et al., Werner et al., 2001, Ann Neurol 50(2): 169-180
Yepes et al., 2009; Trends Neurosci 32(1): 48-55
Zipp et al., 2006, Neurology 67(10): 1880-1883

The invention claimed is:

1. An anti-NMDA receptor monoclonal antibody, which inhibits the interaction between the NMDA receptor and t-PA whereby at least one function of the NMDA receptor is selectively inhibited, wherein said monoclonal antibody comprises the complementarity determining regions (CDRs) having the amino acid sequences consisting of SEQ ID NOs: 29, 30, 31, 32, 33 and 34.

2. The anti-NMDA receptor monoclonal antibody according to claim 1, which comprises a complete heavy chain framework region having an amino acid sequence selected from the group consisting of SEQ ID NOs: 35, 36, 37 and 38 and a complete light chain framework region having an amino acid sequence selected from the group consisting of SEQ ID NOs: 39, 40, 41 and 42.

3. The anti-NMDA receptor monoclonal antibody according to claim 1, which comprises one or two heavy chain variable regions comprising the amino acid sequence of SEQ ID NO: 43 and/or which comprises one or two light chain variable regions comprising the amino acid sequence of SEQ ID NO:44.

4. A pharmaceutical composition comprising the anti-NMDA receptor monoclonal antibody according to claim 1, and one or more components selected from the group consisting of carriers, solvents, diluents, and excipients.

5. The anti-NMDA receptor monoclonal antibody according to claim 1 produced by a deposited hybridoma consisting of 15A4B2E5.

6. The anti-NMDA receptor monoclonal antibody according to claim 1 which is a humanized antibody.

7. An antibody produced by a deposited hybridoma consisting of 15A4B2E5.

8. The antibody according to claim 7 which is a humanized antibody.

* * * * *